United States Patent
Murrish et al.

(10) Patent No.: US 10,628,553 B1
(45) Date of Patent: Apr. 21, 2020

(54) HEALTH INFORMATION TRANSFORMATION SYSTEM

(71) Applicant: Cerner Innovation, Inc., Lenexa, KS (US)

(72) Inventors: John Christopher Murrish, Overland Park, KS (US); Kanakasabha Kailasam, Olathe, KS (US); Douglas S. McNair, Leawood, KS (US); Michael Alan Ash, Parkville, MO (US); Thomas Anthony Fangman, De Soto, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 13/647,187

(22) Filed: Oct. 8, 2012

Related U.S. Application Data

(63) Continuation-in-part of application No. 12/982,143, filed on Dec. 30, 2010, now abandoned.

(60) Provisional application No. 61/545,023, filed on Oct. 7, 2011, provisional application No. 61/641,097, filed on May 1, 2012.

(51) Int. Cl.
  *G06F 19/00* (2018.01)
  *G06F 16/951* (2019.01)
  *G06F 16/22* (2019.01)

(52) U.S. Cl.
  CPC .......... *G06F 19/32* (2013.01); *G06F 16/2228* (2019.01); *G06F 16/951* (2019.01)

(58) Field of Classification Search
  None
  See application file for complete search history.

(56) References Cited

U.S. PATENT DOCUMENTS

| | | | |
|---|---|---|---|
| 4,839,853 A | 6/1989 | Deerwester et al. |
| 5,243,565 A | 9/1993 | Yamamoto |
| 5,301,109 A | 4/1994 | Landauer et al. |
| 5,809,494 A | 9/1998 | Nguyen |

(Continued)

FOREIGN PATENT DOCUMENTS

| | | |
|---|---|---|
| EP | 1043666 A2 | 10/2000 |
| EP | 2365456 A2 | 9/2011 |

(Continued)

OTHER PUBLICATIONS

Aronson, Alan R. "MetaMap: Mapping Text to the UMLS Metathesaurus." (Year: 2006).*

(Continued)

*Primary Examiner* — Charles D Adams
(74) *Attorney, Agent, or Firm* — Shook, Hardy & Bacon L.L.P.

(57) ABSTRACT

Methods, computer systems, and computer readable media for transforming raw healthcare data into relevant healthcare data are provided. Transformation of raw healthcare data into relevant data is accomplished by receiving raw data from a plurality of disparate data sources, indexing the data, and mapping the data. Embodiments transform raw data into relevant data through the use of natural language processing, synonymy and ontology mapping, and adaptive knowledge processing. The relevant data is stored in a one record that includes information necessary to understand and represent that patient.

20 Claims, 14 Drawing Sheets

(56) References Cited

U.S. PATENT DOCUMENTS

| | | | |
|---|---|---|---|
| 5,835,900 A | 11/1998 | Fagg et al. | |
| 6,039,688 A | 3/2000 | Douglas et al. | |
| 6,246,964 B1 | 6/2001 | Blaunstein | |
| 6,246,975 B1 | 6/2001 | Rivonelli et al. | |
| 6,247,004 B1 | 6/2001 | Moukheibir | |
| 6,397,224 B1 | 5/2002 | Zubelida et al. | |
| 6,618,715 B1* | 9/2003 | Johnson et al. | 706/47 |
| 6,654,740 B2 | 11/2003 | Tokuda et al. | |
| 6,665,669 B2 | 12/2003 | Han et al. | |
| 6,996,575 B2 | 2/2006 | Cox et al. | |
| 7,039,634 B2 | 5/2006 | Xu et al. | |
| 7,120,626 B2 | 10/2006 | Li et al. | |
| 7,249,117 B2 | 7/2007 | Estes | |
| 7,440,947 B2 | 10/2008 | Adcock et al. | |
| 7,447,643 B1 | 11/2008 | Olson et al. | |
| 7,496,561 B2 | 2/2009 | Caudill et al. | |
| 7,529,765 B2 | 5/2009 | Brants et al. | |
| 7,555,425 B2 | 6/2009 | Oon | |
| 7,558,778 B2 | 7/2009 | Carus et al. | |
| 7,617,078 B2* | 11/2009 | Rao et al. | 703/2 |
| 7,640,171 B2 | 12/2009 | Gendron et al. | |
| 7,657,540 B1 | 2/2010 | Bayliss | |
| 7,668,820 B2 | 2/2010 | Zuleba | |
| 7,720,846 B1 | 5/2010 | Bayliss | |
| 7,831,423 B2 | 11/2010 | Schubert | |
| 7,844,449 B2 | 11/2010 | Lin et al. | |
| 7,844,566 B2 | 11/2010 | Wnek | |
| 7,853,456 B2 | 12/2010 | Soto et al. | |
| 7,865,373 B2 | 1/2011 | Punzak et al. | |
| 7,899,764 B2 | 3/2011 | Martin et al. | |
| 7,899,796 B1 | 3/2011 | Borthwick et al. | |
| 7,900,052 B2 | 3/2011 | Jonas | |
| 7,912,842 B1 | 3/2011 | Bayliss | |
| 7,933,909 B2 | 4/2011 | Trepetin | |
| 7,953,685 B2 | 5/2011 | Liu et al. | |
| 8,078,554 B2 | 12/2011 | Fung et al. | |
| 8,126,736 B2 | 2/2012 | Anderson et al. | |
| 8,160,895 B2 | 4/2012 | Schmitt et al. | |
| 8,165,893 B1* | 4/2012 | Goldberg et al. | 705/2 |
| 8,200,505 B2 | 6/2012 | Walker et al. | |
| 8,515,777 B1 | 8/2013 | Rajasenan | |
| 8,539,424 B2 | 9/2013 | Tetelbaum | |
| 8,589,424 B1 | 11/2013 | Patel et al. | |
| 8,666,785 B2 | 3/2014 | Baluta et al. | |
| 8,838,628 B2 | 9/2014 | Leighton et al. | |
| 8,856,156 B1 | 10/2014 | McNair et al. | |
| 9,375,142 B2 | 6/2016 | Schultz et al. | |
| 9,542,647 B1 | 1/2017 | Mirhaji | |
| 9,734,146 B1 | 8/2017 | McNair et al. | |
| 10,268,687 B1 | 4/2019 | McNair et al. | |
| 10,431,336 B1 | 10/2019 | Murrish et al. | |
| 2002/0032583 A1 | 3/2002 | Joao | |
| 2002/0035486 A1 | 3/2002 | Huyn et al. | |
| 2002/0038227 A1 | 3/2002 | Fey et al. | |
| 2002/0038308 A1* | 3/2002 | Cappi | G06F 17/30566 |
| 2002/0042793 A1 | 4/2002 | Choi | |
| 2002/0073138 A1 | 6/2002 | Gilbert et al. | |
| 2003/0023571 A1 | 1/2003 | Barnhill | |
| 2003/0038308 A1 | 2/2003 | Kim | |
| 2003/0163057 A1 | 8/2003 | Flick et al. | |
| 2003/0212580 A1 | 11/2003 | Shen | |
| 2004/0199332 A1 | 10/2004 | Iliff | |
| 2004/0230105 A1 | 11/2004 | Geva et al. | |
| 2005/0027562 A1 | 2/2005 | Brown | |
| 2005/0049497 A1 | 3/2005 | Krishnan et al. | |
| 2005/0119534 A1 | 6/2005 | Trost et al. | |
| 2005/0144042 A1 | 6/2005 | Joffe et al. | |
| 2006/0020465 A1 | 1/2006 | Cousineau et al. | |
| 2006/0064447 A1 | 3/2006 | Malkov | |
| 2006/0129427 A1 | 6/2006 | Wennberg | |
| 2006/0161457 A1 | 7/2006 | Rapaport et al. | |
| 2006/0173663 A1 | 8/2006 | Langheier et al. | |
| 2006/0205564 A1 | 9/2006 | Peterson | |
| 2006/0206027 A1 | 9/2006 | Malone | |
| 2006/0206359 A1 | 9/2006 | Stang | |
| 2006/0218010 A1 | 9/2006 | Michon et al. | |
| 2006/0271556 A1 | 11/2006 | Mukherjee et al. | |
| 2007/0005621 A1 | 1/2007 | Lesh et al. | |
| 2007/0026365 A1 | 2/2007 | Friedrich et al. | |
| 2007/0031873 A1 | 2/2007 | Wang et al. | |
| 2007/0094048 A1 | 4/2007 | Grichnik | |
| 2007/0106533 A1 | 5/2007 | Greene | |
| 2007/0106752 A1 | 5/2007 | Moore | |
| 2007/0233391 A1 | 10/2007 | Milstein et al. | |
| 2007/0239482 A1 | 10/2007 | Finn et al. | |
| 2007/0244724 A1 | 10/2007 | Pendergast et al. | |
| 2008/0021288 A1 | 1/2008 | Bowman et al. | |
| 2008/0046292 A1 | 2/2008 | Myers et al. | |
| 2008/0097938 A1 | 4/2008 | Guyon et al. | |
| 2008/0131374 A1 | 6/2008 | Medich et al. | |
| 2008/0133269 A1 | 6/2008 | Ching | |
| 2008/0147441 A1 | 6/2008 | Kil | |
| 2008/0172214 A1 | 7/2008 | Col et al. | |
| 2008/0172251 A1 | 7/2008 | Reichert et al. | |
| 2008/0183454 A1 | 7/2008 | Barabasi et al. | |
| 2008/0195422 A1 | 8/2008 | Nessinger et al. | |
| 2008/0243548 A1 | 10/2008 | Cafer | |
| 2008/0249376 A1 | 10/2008 | Zaleski et al. | |
| 2008/0255884 A1 | 10/2008 | Carus et al. | |
| 2008/0256006 A1* | 10/2008 | Buscema et al. | 706/13 |
| 2008/0268413 A1 | 10/2008 | Leichner | |
| 2008/0275731 A1 | 11/2008 | Rao et al. | |
| 2008/0287746 A1 | 11/2008 | Reisman | |
| 2008/0288292 A1 | 11/2008 | Bi et al. | |
| 2008/0288474 A1 | 11/2008 | Chin et al. | |
| 2008/0294692 A1 | 11/2008 | Angell et al. | |
| 2008/0301177 A1* | 12/2008 | Doherty | G06F 17/30864 |
| 2008/0306926 A1 | 12/2008 | Friedlander et al. | |
| 2009/0006431 A1 | 1/2009 | Agrawal et al. | |
| 2009/0012928 A1 | 1/2009 | Lussier et al. | |
| 2009/0112892 A1* | 4/2009 | Cardie | G06F 17/30719 |
| 2009/0125333 A1 | 5/2009 | Heywood et al. | |
| 2009/0132284 A1 | 5/2009 | Fey et al. | |
| 2009/0164249 A1 | 6/2009 | Hunt et al. | |
| 2009/0259493 A1 | 10/2009 | Venon et al. | |
| 2009/0299977 A1 | 12/2009 | Rosales | |
| 2009/0304246 A1 | 12/2009 | Walker et al. | |
| 2009/0318775 A1 | 12/2009 | Michelson et al. | |
| 2009/0319295 A1* | 12/2009 | Kass-Hout et al. | 705/2 |
| 2010/0082369 A1 | 4/2010 | Prenelus et al. | |
| 2010/0088117 A1 | 4/2010 | Belden et al. | |
| 2010/0121883 A1 | 5/2010 | Cutting et al. | |
| 2010/0131438 A1 | 5/2010 | Pandya et al. | |
| 2010/0131482 A1 | 5/2010 | Linthicum et al. | |
| 2010/0131883 A1 | 5/2010 | Linthicum et al. | |
| 2010/0142774 A1 | 6/2010 | Ben-Haim et al. | |
| 2010/0145720 A1 | 6/2010 | Reiner | |
| 2010/0179818 A1 | 7/2010 | Kelly et al. | |
| 2010/0185685 A1 | 7/2010 | Chew et al. | |
| 2010/0274576 A1 | 10/2010 | Young | |
| 2010/0293003 A1 | 11/2010 | Abbo | |
| 2010/0299155 A1 | 11/2010 | Findlay et al. | |
| 2010/0324861 A1 | 12/2010 | Goulding et al. | |
| 2010/0324938 A1 | 12/2010 | Ennett et al. | |
| 2011/0010401 A1 | 1/2011 | Adams et al. | |
| 2011/0015937 A1 | 1/2011 | Janas et al. | |
| 2011/0046979 A1 | 2/2011 | Tulipano et al. | |
| 2011/0067108 A1 | 3/2011 | Hoglund | |
| 2011/0077973 A1 | 3/2011 | Breitenstein et al. | |
| 2011/0087501 A1 | 4/2011 | Severin | |
| 2011/0093467 A1 | 4/2011 | Sharp et al. | |
| 2011/0119089 A1* | 5/2011 | Carlisle | 705/3 |
| 2011/0161110 A1 | 6/2011 | Mault | |
| 2011/0201900 A1 | 8/2011 | Zhang et al. | |
| 2011/0225001 A1 | 9/2011 | Shen | |
| 2011/0246238 A1 | 10/2011 | Vdovjak et al. | |
| 2011/0270629 A1 | 11/2011 | Abbo | |
| 2011/0295621 A1 | 12/2011 | Farooq et al. | |
| 2011/0306845 A1 | 12/2011 | Osorio | |
| 2012/0020536 A1 | 1/2012 | Moehrle | |
| 2012/0047105 A1 | 2/2012 | Saigal et al. | |
| 2012/0059779 A1 | 3/2012 | Syed et al. | |
| 2012/0072235 A1 | 3/2012 | Varadarajan et al. | |
| 2012/0078127 A1 | 3/2012 | McDonald et al. | |

(56) References Cited

U.S. PATENT DOCUMENTS

| | | |
|---|---|---|
| 2012/0086963 A1 | 4/2012 | Fujitsuka et al. |
| 2012/0089420 A1 | 4/2012 | Hoffman et al. |
| 2012/0089421 A1 | 4/2012 | Hoffman et al. |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | McErlane |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2012/0246102 A1 | 9/2012 | Sudharsan |
| 2013/0006911 A1 | 1/2013 | Christie, IV et al. |
| 2013/0023434 A1 | 1/2013 | Van Laar |
| 2013/0046529 A1 | 2/2013 | Grain et al. |
| 2013/0046558 A1 | 2/2013 | Landi et al. |
| 2013/0110547 A1 | 5/2013 | Englund et al. |
| 2013/0110548 A1 | 5/2013 | Kutty |
| 2013/0132312 A1 | 5/2013 | Lee et al. |
| 2013/0132323 A1 | 5/2013 | Soto et al. |
| 2013/0197938 A1 | 8/2013 | Bayouk et al. |
| 2013/0245389 A1 | 9/2013 | Schultz et al. |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | McNair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0124269 A1 | 5/2017 | McNair et al. |

FOREIGN PATENT DOCUMENTS

| | | |
|---|---|---|
| WO | 2012122195 A1 | 9/2012 |
| WO | 2012122196 A1 | 9/2012 |

OTHER PUBLICATIONS

Preinterview First Action Interview in U.S. Appl. No. 12/982,143 dated Oct. 4, 2012, 10 pages.
Preinterview First Action Interview in U.S. Appl. No. 12/982,131 dated Sep. 26, 2012, 42 pages.
Final Office Action in U.S. Appl. No. 12/982,131 dated Apr. 24, 2013, 53 pages.
Final Office Action in U.S. Appl. No. 12/982,143 dated May 1, 2013, 36 pages.
Final Office Action in U.S. Appl. No. 12/982,137 dated May 8, 2013, 45 pages.
Non-Final Office Action in U.S. Appl. No. 12/982,143 dated Oct. 2, 2013, 32 pages.
Non-Final Office Action dated Dec. 20, 2013 in U.S. Appl. No. 12/982,131, 19 pages.
Final Office Action dated Nov. 7, 2014 in U.S. Appl. No. 12/982,131, 17 pages.
Notice of Allowance dated Apr. 9, 2015 in U.S. Appl. No. 12/982,131, 12 pages.
Final Office Action dated Dec. 4, 2015 in U.S. Appl. No. 13/963,732, 21 pages.
First Action Interview Office Action dated Dec. 3, 2015 in U.S. Appl. No. 14/147,978, 8 pages.
First Action Interview Office Action dated Jan. 20, 2016 in U.S. Appl. No. 14/147,991, 8 pages.
First Action Interview Office Action dated Jan. 15, 2016 in U.S. Appl. No. 14/148,002, 8 pages.
First Action Interview Office Action dated Jan. 6, 2016 in U.S. Appl. No. 14/148,020, 8 pages.
First Action Interview Office Action dated Dec. 22, 2015 in U.S. Appl. No. 14/148,028, 8 pages.
First Action Interview Office Action dated Nov. 19, 2015 in U.S. Appl. No. 14/148,039, 8 pages.
First Action Interview Preinterview Communication dated Nov. 19, 2015 in U.S. Appl. No. 14/148,046, 5 pages.
First Action Interview Office Action dated Jan. 22, 2016 in U.S. Appl. No. 14/148,050, 8 pages.
First Action Interview Office Action dated Dec. 17, 2015 in U.S. Appl. No. 14/148,059, 8 pages.
Ohno-Machado, Lucila; "Realizing the full potential of electronic health records: the role of natural language processing", Sep. 2011, Journal of American Medical Information Association, vol. 18 No. 5, p. 539.
First Action Interview Preinterview Communication dated Jan. 3, 2013 in U.S. Appl. No. 13/250,072, 4 pages.
First Action Interview Office Action dated Oct. 8, 2013 in U.S. Appl. No. 13/250,072, 5 pages.
Final Office Action dated Jun. 2, 2014 in U.S. Appl. No. 13/250,072, 14 pages.
Non-Final Office Action dated Mar. 2, 2015 in U.S. Appl. No. 13/250,072, 14 pages.
Final Office Action dated Sep. 28, 2015 in U.S. Appl. No. 13/250,072, 15 pages.
First Action Interview Pre-Interview Communication dated Feb. 10, 2014 in U.S. Appl. No. 13/269,244, 5 pages.
First Action Interview Office Action dated Jun. 17, 2014 in U.S. Appl. No. 13/269,244, 5 pages.
Non-Final Office Action dated Dec. 5, 2014 in U.S. Appl. No. 13/269,244, 18 pages.
Final Office Action dated Jul. 13, 2015 in U.S. Appl. No. 13/269,244, 21 pages.
First Action Interview Pre-Interview Communication dated Mar. 28, 2013 in U.S. Appl. No. 13/269,262, 4 pages.
First Action Interview Office Action dated Oct. 11, 2013 in U.S. Appl. No. 13/269,262, 5 pages.
Final Office Action dated Jun. 2, 2014 in U.S. Appl. No. 13/269,262, 15 pages.
Non-Final Office Action dated May 22, 2015 in U.S. Appl. No. 13/963,732, 14 pages.
Non-Final Office Action dated Sep. 1, 2015 in U.S. Appl. No. 13/874,961, 33 pages.
Christian Roever, Package 'bspec', Feb. 21, 2013, r-project.org, pp. 1-27.
International Search Report and Written Opinion dated Nov. 26, 2014 in Application No. PCT/US2014/050735, 11 pages.
First Action Interview Preinterview Communication dated Jun. 30, 2015 in U.S. Appl. No. 14/147,978, 5 pages.
First Action Interview Preinterview Communication dated Jul. 30, 2015 in U.S. Appl. No. 14/147,991, 5 pages.
First Action Interview Pre-Interview Communication dated Aug. 11, 2015 in U.S. Appl. No. 14/148,002, 5 pages.
First Action Interview Preinterview Communication dated Aug. 13, 2015 in U.S. Appl. No. 14/148,020, 5 pages.
First Action Interview Preinterview Communication dated Jun. 30, 2015 in U.S. Appl. No. 14/148,028, 5 pages.
First Action Interview Preinterview Communication dated Jul. 17, 2015 in U.S. Appl. No. 14/148,039, 5 pages.
First Action Interview Preinterview Communication dated Aug. 14, 2015 in U.S. Appl. No. 14/148,050, 5 pages.
First Action Interview Preinterview Communication dated Aug. 11, 2015 in U.S. Appl. No. 14/148,059, 5 pages.
Non-Final Office Action dated Aug. 5, 2015 in U.S. Appl. No. 14/477,284, 11 pages.
Notice of Allowance dated Jun. 4, 2014 in U.S. Appl. No. 13/645,896, 12 pages.
Abbott A, Tsay A. Sequence Analysis and Optimal Matching Methods in Sociology, Review and Prospect. Sociol Meth Res 2000;29:3-33.

(56) References Cited

OTHER PUBLICATIONS

Agrawal R, et al. 'Fast Discovery of Association Rules.' in Fayyad U, et al., eds., Advances in Knowledge Discovery and Data Mining, pp. 307-328. Menlo Park, AAAI Press, 1996.
Berchtold A, Raftery A. The Mixture Transition Distribution Model for High-Order Markov Chains and Non-Gaussian Time Series. Stat Sci 2002;17:328-56.
Billari F, et al. Timing, Sequencing, and quantum of Life Course Events: A Machine-Learning Approach. Eur J Pop 2006;22:37-65.
Deville J, Saporta G. Correspondence Analysis with an Extension Towards Nominal Time Series. J Econometrics 1983;22:169-89.
Dijkstra W, Taris T. Measuring the Agreement Between Sequences. Sociol Meth Res 1995;24:214-31.
Dvorak J, et al. Risk Factor Analysis for Injuries in Football Players: Possibilities for a Prevention Program. Am J Sports Med. 2000;28:S69-74.
Dvorak J, Junge A. Football Injuries and Physical Symptoms: A Review of the Literature. Am J Sports Med 2000;28:S3-9.
Han J-W, et al. Frequent Pattern Mining: Current status and future directions. Data Mining and Knowledge Discovery 2007;15:55-86.
Hawkins R, Fuller C. A Prospective Eidemiological Study of Injuries in Four English Professional Football Clubs. Br J Sports Med 1999;33:196-203.
Junge A, Dvorak J. Soccer Injuries: A Review on Incidence and Prevention. Sports Med. 2004;34:929-38.
Nielsen A, Yde J. Epidemiology and Traumatology of Injuries in Soccer. Am J Sports Med 1989;17:803-7.
Zaki M. Spade: An Efficient Algorithm for Mining Frequent Sequences. Machine Learning 2001;42:31-60.
Huyse, Frits et al., Compri-An Instrument to Detect Patients With Complex Care Needs; Psychosomatics 42:3, May-Jun. 2001; 7 pages.
Berry, Leonard et al., Care Coordination for Patients With Complex Health Profiles in Inpatients and Outpatient Settings; Mayo Clinic Proceedings; www.mayoclinicproceedings.org; Jan. 11, 2013; 11 pages.
Cohen, Eyal et al., Integrated Complex Care Coordination for Children With Medical Complexity: A Mixed-Methods Evaluation of Tertiary Care-Community Collaboration; BioMed Central The Open Access Publisher; www.biomedcentral.com/1472-6963/12/366; Oct. 23, 2012; 23 pages.
Nealon, et al.: Agent-Based Applications in Health Care, Department of Computing, Oxford Brookes University and Computer Science and Mathematics Department, University Rovira I Virgill, 17 pages.
Kang, et al.: Mining Based Decision Support Multi-agent System for Personalized e-Healthcare Service*, Schook of Computer Engineering, Sungkyunkwan University, 10 pages.
Mabry, et al.: Clinical Decision Support with IM-Agents and ERMA Multi-agents, Department of Computer Science and Emergency Medicine, 6 pages.
Murat Sariyar and Andreas Borg, The Recordlinkage Package: Detecting Errors in Data, Dec. 2010, The R Journal vol. 212, pp. 61-67.
Final Office Action dated Sep. 8, 2016 in U.S. Appl. No. 14/148,002, 24 pages.
Final Office Action dated Sep. 9, 2016 in U.S. Appl. No. 14/148,050, 23 pages.
Final Office Action dated Sep. 23, 2016 in U.S. Appl. No. 14/148,059, 27 pages.
Final Office Action dated Sep. 26, 2016 in U.S. Appl. No. 13/269,244, 35 pages.
Final Office Action dated Oct. 3, 2016 in U.S. Appl. No. 14/148,046, 26 pages.
Final Office Action dated Nov. 2, 2016 in U.S. Appl. No. 13/874,961, 18 pages.
International Preliminary Report on Patentability dated Feb. 25, 2016 in Application No. PCT/US2014/050735, 9 pages.
First Action Interview Office Action dated Feb. 26, 2016 in U.S. Appl. No. 14/148,046, 8 pages.
First Action Interview Preinterview Communication dated Mar. 10, 2016 in U.S. Appl. No. 14/175,750, 4 pages.
Non-Final Office Action dated Mar. 10, 2016 in U.S. Appl. No. 13/269,244, 28 pages.
Notice of Allowance dated Mar. 11, 2016 in U.S. Appl. No. 14/477,284, 6 pages.
Non-Final Office Action dated Mar. 30, 2016 in U.S. Appl. No. 13/250,072, 12 pages.
Final Office Action dated Jun. 28, 2016 in U.S. Appl. No. 13/874,961, 19 pages.
Final Office Action dated Jul. 1, 2016 in U.S. Appl. No. 14/147,978, 25 pages.
Final Office Action dated Jul. 14, 2016 in U.S. Appl. No. 14/148,028, 28 pages.
Final Office Action dated Jul. 20, 2016 in U.S. Appl. No. 14/148,039, 32 pages.
Non-Final Office Action dated Jul. 26, 2016 in U.S. Appl. No. 13/963,732, 16 pages.
Final Office Action dated Jul. 29, 2016 in U.S. Appl. No. 14/148,020, 23 pages.
Notice of Allowance dated Aug. 2, 2016 in U.S. Appl. No. 14/477,284, 7 pages.
Final Office Action dated Aug. 15, 2016 in U.S. Appl. No. 14/147,991, 34 pages.
First Action Interview Office Action dated Aug. 17, 2016 in U.S. Appl. No. 14/175,750, 5 pages.
Non-Final Office Action dated Sep. 1, 2016 in U.S. Appl. No. 14/209,568, 12 pages.
Final Office Action dated Dec. 15, 2016 in U.S. Appl. No. 13/250,072, 18 pages.
Final Office Action dated Feb. 16, 2017 in U.S. Appl. No. 14/175,750, 18 pages.
European Search Report dated Mar. 13, 2017 in European Patent Application No. 14835964, 9 pages.
Final Office Action dated May 12, 2017 in U.S. Appl. No. 13/963,732, 20 pages.
Non-Final Office Action dated May 18, 2017 in U.S. Appl. No. 14/147,978, 29 pages.
Non-Final Office Action dated Sep. 21, 2017 in U.S. Appl. No. 14/148,046, 28 pages.
Non-Final Office Action dated Sep. 22, 2017 in U.S. Appl. No. 14/175,750, 17 pages.
Non-Final Office Action dated Oct. 2, 2017 in U.S. Appl. No. 13/250,072, 8 pages.
Kiran, R. Uday, and P. Krishna Re. "An improved multiple minimum support based approach to mine rare association rules." Computational Intelligence and Data Mining, 2009. CIDM'09. IEEE Symposium on. IEEE, 2009.
Non-Final Office Action dated Jun. 6, 2017 in U.S. Appl. No. 14/148,059, 30 pages.
Final Office Action dated Jun. 16, 2017 in U.S. Appl. No. 14/209,568, 20 pages.
First Action Interview Preinterview Communication dated Jun. 21, 2017 in U.S. Appl. No. 14/281,593, 4 pages.
Non-Final Office Action dated Jun. 21, 2017 in U.S. Appl. No. 14/148,039, 34 pages.
Non-Final Office Action dated Jun. 28, 2017 in U.S. Appl. No. 14/148,046, 31 pages.
Non-Final Office Action dated Jul. 5, 2017 in U.S. Appl. No. 14/147,991, 36 pages.
Non-Final Office Action dated Jul. 24, 2017 in U.S. Appl. No. 14/148,020, 22 pages.
Supplemental Notice of Allowability dated Jul. 26, 2017 in U.S. Appl. No. 14/477,284, 6 pages.
Final Office Action dated Jul. 27, 2017 in U.S. Appl. No. 13/647,187, 23 pages.
Non-Final Office Action dated Jul. 31, 2017 in U.S. Appl. No. 14/148,060, 24 pages.
Non-Final Office Action dated Aug. 10, 2017 in U.S. Appl. No. 14/148,002, 26 pages.
First Action Interview Office Action dated Sep. 6, 2017 in U.S. Appl. No. 14/281,593, 7 pages.

(56) References Cited

OTHER PUBLICATIONS

First Action Interview Pre-Interview Communication dated Dec. 8, 2017 in U.S. Appl. No. 14/792,736, 22 pages.
Final Office Action dated Dec. 11, 2017 in U.S. Appl. No. 14/148,059, 27 pages.
Non-Final Office Action dated Dec. 27, 2017 in U.S. Appl. No. 13/963,732, 18 pages.
Final Office Action dated Jan. 4, 2018 in U.S. Appl. No. 14/147,991, 35 pages.
Final Office Action dated Jan. 5, 2018 in U.S. Appl. No. 14/148,028, 32 pages.
Final Office dated Jan. 18, 2018 in U.S. Appl. No. 14/147,978, 28 pages.
Final Office Action dated Jan. 26, 2018 in U.S. Appl. No. 14/148,039, 33 pages.
Final Office Action dated Feb. 16, 2018 in U.S. Appl. No. 14/281,593, 15 pages.
Non-Final Office Action dated Mar. 2, 2018 in U.S. Appl. No. 14/209,568, 23 pages.
Final Office Action dated Apr. 2, 2018 in U.S. Appl. No. 14/148,020, 21 pages.
Final Office Action dated Apr. 2, 2018 in U.S. Appl. No. 14/148,050, 24 pages.
First Action Interview Office Action dated Apr. 17, 2018 in U.S. Appl. No. 14/792,736, 24 pages.
Final Office Action dated May 1, 2018 in U.S. Appl. No. 14/148,046, 31 pages.
Non-Final Office Action dated May 3, 2018 in U.S. Appl. No. 15/392,928, 15 pages.
Final Office Action dated May 30, 2018 in U.S. Appl. No. 14/148,002, 29 pages.
Final Office Action dated May 31, 2018 in U.S. Appl. No. 13/250,072, 20 pages.
Office Action dated Dec. 29, 2017 in U.S. Appl. No. 14/555,058, 14 pages.
Final Office Action dated Jun. 13, 2018 in U.S. Appl. No. 14/175,750, 11 pages.
Office Action dated Jun. 28, 2018 in U.S. Appl. No. 14/148,059, 27 pages.
Final Office Action dated Jun. 29, 2018 in U.S. Appl. No. 13/963,732, 22 pages.
Final Office Action dated Sep. 7, 2018 in U.S. Appl. No. 14/555,058, 19 pages.
Final Office Action received for U.S. Appl. No. 14/792,736, dated Oct. 15, 2018, 18 pages.
Non-Final Office Action received for U.S. Appl. No. 14/147,978, dated Sep. 28, 2018, 29 pages.
Notice of Allowance received for U.S. Appl. No. 13/874,961, dated Oct. 15, 2018, 9 pages.
Non-Final Office Action received for U.S. Appl. No. 14/148,059, dated Apr. 26, 2019, 28 pages.
Non-Final Office Action received for U.S. Appl. No. 14/792,736, dated Apr. 11, 2019, 18 pages.
Non-Final Office Action received for U.S. Appl. No. 14/982,982, dated May 14, 2019, 9 pages.
Arpaia et al., "Multi-Agent Remote Predictive Diagnosis of Dangerous Good Transports", Instrumentation and Measurement Technology Conference, Proceedings of the IEEE, May 17-19, 2005, pp. 1685-1690.
Non-Final Office Action received for U.S. Appl. No. 14/555,058, dated Jun. 25, 2019, 20 pages.
Non-Final Office Action received for U.S. Appl. No. 13/963,732, dated Jul. 11, 2019, 13 pages.
Non-Final Office Action received for U.S. Appl. No. 14/148,046, dated Jun. 24, 2019, 27 pages.
Non-Final Office Action received for U.S. Appl. No. 14/147,991, dated Nov. 27, 2018, 37 pages.
Final Office Action received for U.S. Appl. No. 14/148,020, dated Oct. 9, 2019, 25 pages.
Preinterview First Office Action received for U.S. Appl. No. 15/855,720, dated Oct. 3, 2019, 4 pages.
First Action Interview Office Action received for U.S. Appl. No. 15/386,876, dated Jan. 28, 2020, 24 pages.
Final Office Action received for U.S. Appl. No. 14/555,058, dated Feb. 12, 2020, 22 pages.

\* cited by examiner

FIG. 5.

DOE, JOHN  GENDER: MALE  DOB: JULY 09, 1996  AGE: 14 YEARS  MRN: 12A23B

HOME | MY PATIENTS

PROGRAM SUMMARY | ASSESSMENTS | HIE SUMMARY

DIABETES CLINICAL QUALITY MEASURES

- [6.3] HEMOGLOBIN A1C < 7 (%)
  1 WEEK AGO    NORTHLINE CLINIC
  DUE: 03/29/2011

- [95] LDL < 100 (MG/DL)
  1 WEEK AGO    NORTHLINE CLINIC
  DUE: 03/29/2011

- [131/83] BLOOD PRESSURE < 130/80 (MMHG)
  1 WEEK AGO  NORTHLINE CLINIC
  DUE: 03/29/2011

- [145] TRIGLYCERIDES < 150 (MG/DL)
  1 WEEK AGO    NORTHLINE CLINIC
  DUE: 09/30/2011

- [123] FOOT EXAM DONE
  1 WEEK AGO    NORTHLINE CLINIC
  DUE: 09/30/2011

- [COMPLETE] EYE EXAM DONE
  1 WEEK AGO    NORTHLINE CLINIC
  DUE: 09/30/2011

- [COMPLETE] FOOT EXAM DONE
  1 WEEK AGO    NORTHLINE CLINIC
  DUE: 09/30/2011

- [NOT MET] DIET COUNSELING DONE
  1 WEEK AGO NORTHLINE CLINIC
  DUE: 09/30/2011

SEMANTIC SEARCH
- ✚ NEW SEARCH
- DIABETES, MEDICATION
- DIET
- ENDOCRINOLOGY
- EYE EXAM
- FOOT MONOFILAMENT, VISUAL, PEDAL PULSE
- GLUCOSE
- HEMOGLOBIN A1C
- LIPID PROFILE
- OBESITY
- RETINOPATHY
- TOBACCO
- TYPE 2 DIABETES

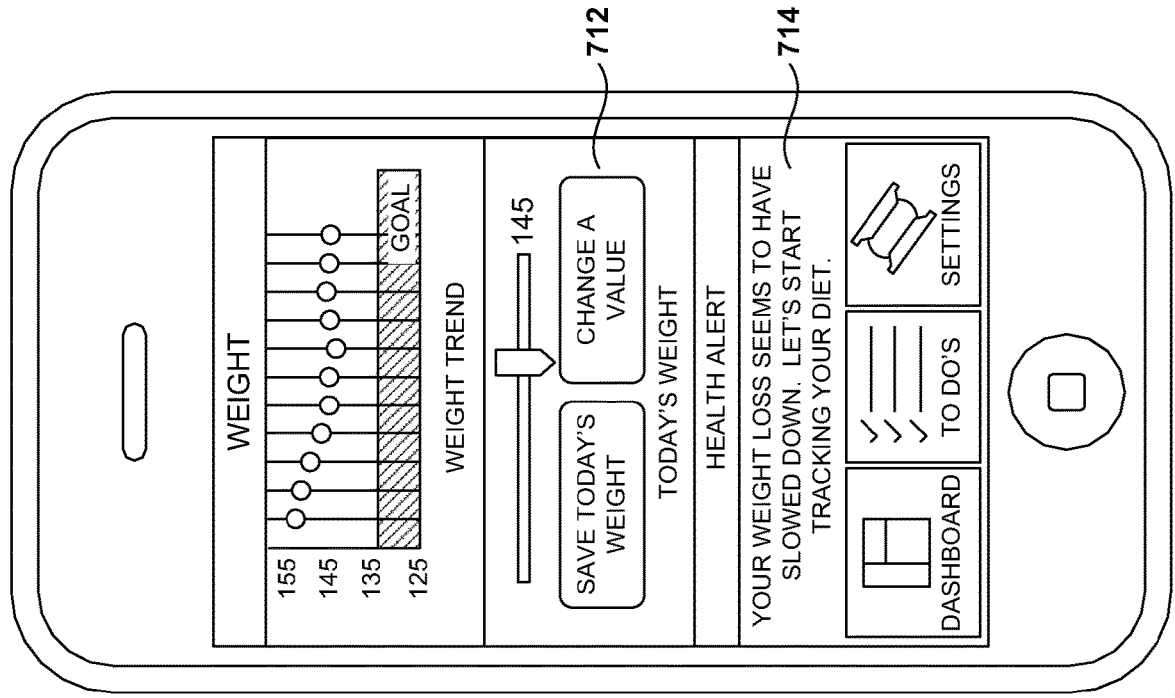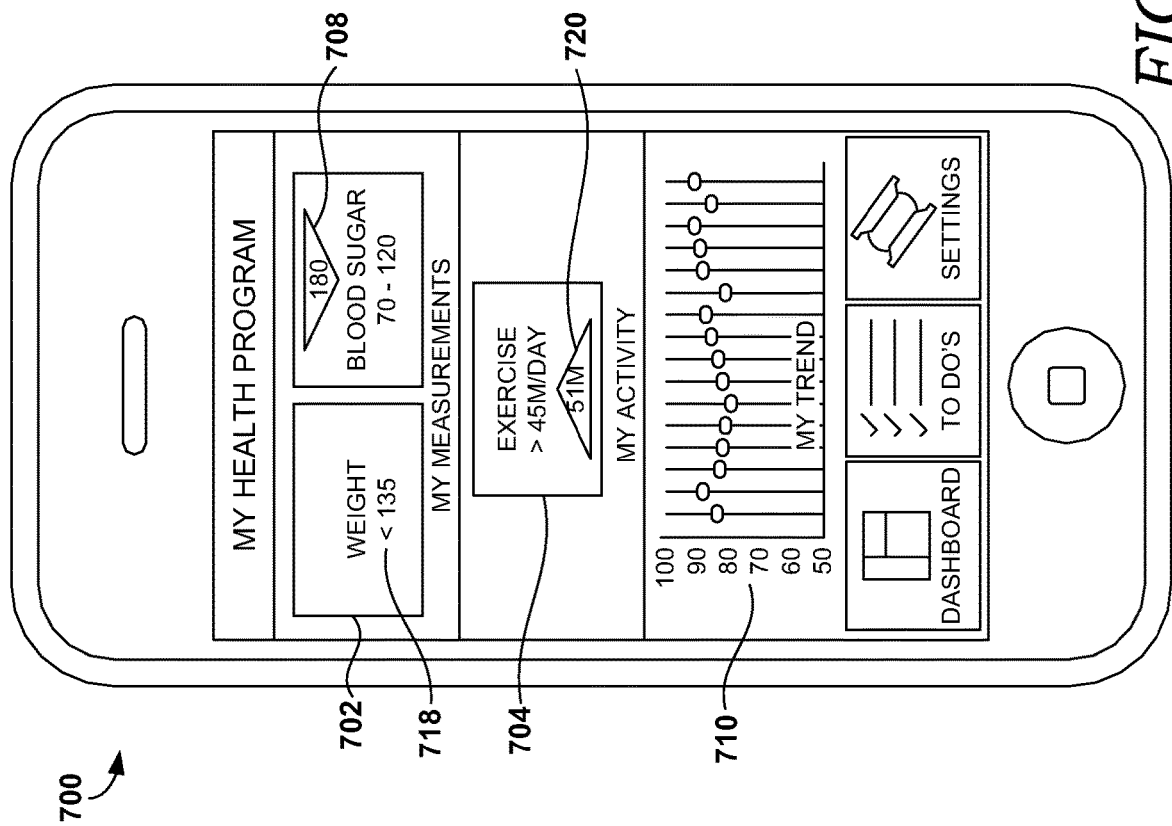
FIG. 7.

EXAMPLE WITH SEPSIS AGENT

HEALTH INFORMATION TRANSFORMATION SYSTEM

CROSS-REFERENCE TO RELATED APPLICATIONS

This application claims the benefits of U.S. Provisional Application No. 61/545,023, titled "Health Information Transformation System," filed Oct. 7, 2011; U.S. Provisional Application No. 61/641,097, titled "System and Method for Record Linkage," filed May 1, 2012; and U.S. application Ser. No. 12/982,143, titled "Health Information Transformation System," filed Dec. 30, 2010, each of which is hereby expressly incorporated by reference in its entirety.

INTRODUCTION

Traditionally, although a wealth of healthcare data exists with respect to a particular patient, the data is not in a form that easily utilized by computer applications. As well, the healthcare data is often dispersed throughout multiple sources, and it is difficult to assimilate and relate the same clinical concept from these multiple sources. Additionally, provider or patient graphical user interfaces that utilize this healthcare data are not user-friendly or, in the case of provider graphical user interfaces, do not present the provider with a comprehensive view of a patient's state of health.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Examples of the present invention are directed to methods, computer systems, and computer-readable media for use in transforming raw healthcare data and health care information from disparate sources into relevant healthcare data that may be utilized by a variety of healthcare applications. This transformation process occurs in a health information transformation system. The ability to transform raw healthcare data into relevant healthcare data, which then may be used, for example, to facilitate patient care and management, is an important advantage in the never-ending quest to improve the quality of healthcare.

In one aspect of the invention, raw data is received from a plurality of data collectors, where the plurality of data collectors extract raw data from a plurality of raw data sources. In one aspect, the plurality of data collectors comprise electronic medical records crawlers, clinical and administrative data collectors, claims data collectors, document feed collectors and medical device feed collectors. In turn, the plurality of raw data sources may comprise electronic medical records, images, claims, data from patients or providers, documents, and medical devices. The raw data is sorted into unstructured raw data, structured data of non-standard nomenclature, and structured data of standard nomenclature. The sorted data is then transformed into relevant data through the use of natural language processing where needed, synonym discovery (synonymic matching), nomenclature, and ontology mapping, and distributed adaptive knowledge processing. The relevant data is loaded into a "one record" data repository, which may comprise a plurality of repositories and computer applications, including provider and patient care cards, and made accessible to a number of services. In some embodiments, the plurality of data repositories may comprise real time transaction processing data repository, online analytical processing data repository, data mart data repository, search index data repository, and custom data repository. In embodiments the one record repository facilitates provider interaction services, consumer engagement services, population research (including identified and de-identified patient population research), and other services.

BRIEF DESCRIPTION OF THE DRAWINGS

Embodiments are described in detail below with reference to the attached drawing figures, wherein:

FIGS. 4-6 depict exemplary graphical user interfaces of provider care cards in accordance with embodiments of the present invention;

FIG. 7 depicts an exemplary graphical user interface of a patient care card in accordance with an embodiment of the present invention.

DETAILED DESCRIPTION

Figure 1A:
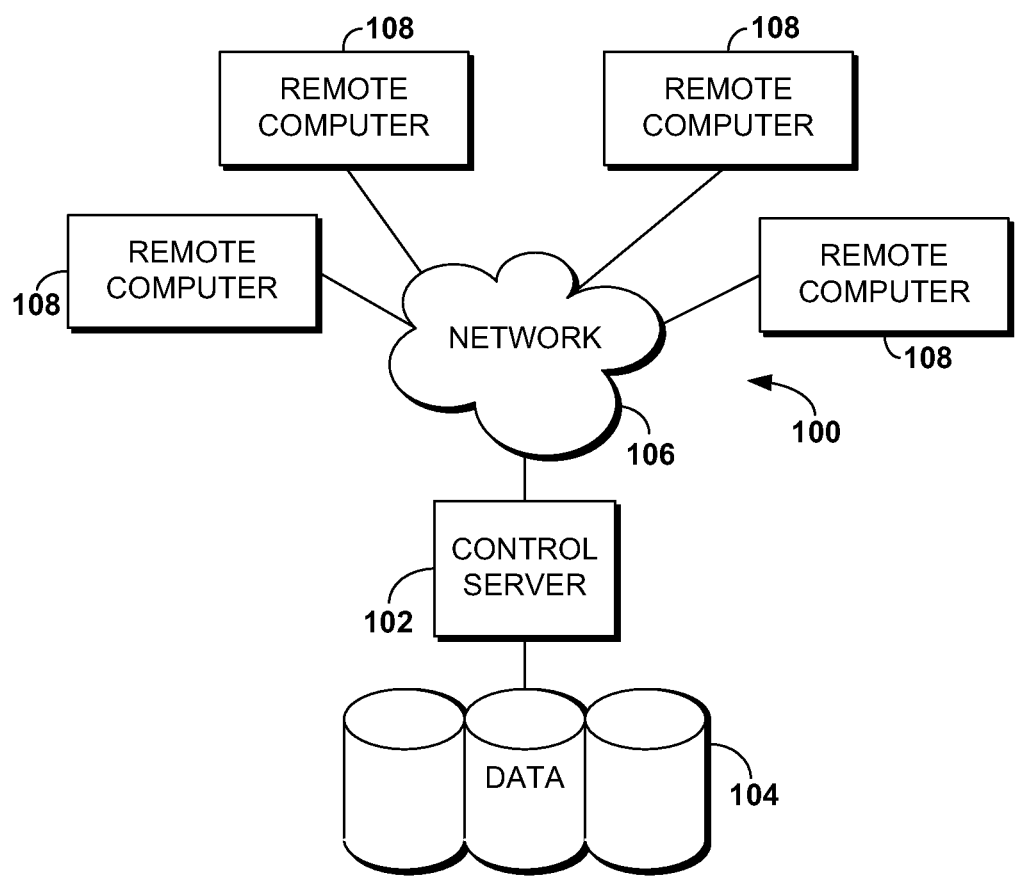
FIG. 1A is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Embodiments of the invention are directed to methods, computer systems, and computer-readable media for use in transforming raw healthcare data into relevant healthcare data that may be utilized by a variety of healthcare applications. In some embodiments the data is transformed into a dataset (referred to as "one record") which includes data and or pointers to data about a particular patient, from available data sources. The one record thereby facilitates the mining of patient data by making disparate data accessible, searchable, updatable, and usable for treatment, health-care management, and research. The transformation process takes place in a health information transformation system.

As well, embodiments of the invention are directed to graphical user interfaces in the form of provider care cards and patient care cards. Provider and patient care cards are built upon the relevant data generated by the health information transformation system. Provider care cards are user-friendly, intuitive graphical user interfaces that give providers a variety of tools they can use to more effectively care for their patients and improve the quality of healthcare they deliver. As well, patient care cards are also easy-to-use graphical user interfaces that help patients to partner with their providers and assume a more active role in managing their health. The ability to transform raw healthcare data into relevant healthcare data, which then may be used, for example, to facilitate patient care through the use of provider and patient care cards, is an important advantage in the never-ending quest to improve the quality of healthcare.

In one aspect of the invention, raw data is received from a plurality of data collectors, where the plurality of data collectors extract raw data from a plurality of raw data sources. In one aspect, the plurality of data collectors comprise electronic medical records crawlers, clinical and administrative data collectors, claims data collectors, document feed collectors and medical device feed collectors. In turn, the plurality of raw data sources may comprise electronic medical records, personal health records, images, documents, and medical devices. The raw data is sorted into unstructured raw data, structured data of non-standard nomenclature, and structured data of standard nomenclature. The raw data is then transformed into relevant data through the use of natural language processing, nomenclature and ontology mapping, and distributed adaptive knowledge processing. The relevant data is loaded into a plurality of data repositories, and computer applications, including provider and patient care cards, are provided access to the plurality of data repositories. The plurality of data repositories may comprise real time transaction processing data repository, online analytical processing data repository, data mart data repository, search index data repository, and custom data repository.

In another aspect of the invention, a graphical user interface comprising a provider care card is provided. In one aspect, the provider care card comprises a requirements display area configured to display at least one or more clinical measures relating to at least one patient, and a measurements display area configured to display one or more measurements completed for one or more of the clinical measures. In addition, the invention comprises a first plurality of microdisplays configured to display a visual indicator for each of the clinical measures that has been met, and a second plurality of microdisplays configured to display a visual indicator for each of the clinical measures that has not been met. In another aspect, along with the features outlined above, the provider care card also comprises the first plurality of microdisplays and the second plurality of microdisplays arranged over a time period ranging from at least an initial point of provider/patient contact to at least a current point of provider/patient contact regardless of whether the clinical measure has been met or not met. In yet another aspect, along with the features outlined above, the first plurality of microdisplays are shaded a first color to indicate the clinical measure has been met, and the second plurality of microdisplays are shaded a second color to indicate the clinical measure has not been met.

In yet another aspect of the invention, a graphical user interface comprising a patient care card is provided. In one aspect, the patient care card comprises a requirements display area configured to display at least one or more clinical measures relating to a patient, and a visual indicator that changes depending on whether the clinical measure has been met. In another aspect, the patient care card comprises a requirements display area configured to display at least one or more clinical measures relating to a patient, and a measurements display area configured to display one or more measurements completed for one or more of the clinical measures relating to the patient. A trend display area is also provided that is configured to display at least one or more graphical representations of the clinical measures relating to the patient. As well, a visual indicator is provided that changes depending on whether the one or more clinical measures has been met. In yet another aspect of the invention, the patient care card comprises a patient input display area configured to receive inputs from the patient, where the inputs correspond to at least one or more of the clinical measures relating to the patient. The patient input display area is in addition to the requirements display area, measurements display area, trend display area and visual indicator as outlined above.

Having briefly described embodiments of the present invention, an exemplary operating environment suitable for use in implementing embodiments of the present invention is described below. FIG. 1A provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform, as further described in connection to FIG. 1B.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices. In some embodiments, remote computers 108 comprise computing-devices that are part of a cloud-computing platform. In some embodiments, a remote computer 108 is associated with a health records, data source such as an electronic health record (EHR) system of a hospital or medical organization (such as medical organization 156 of FIG. 1B), a health information exchange EHR, insurance provider EHR, ambulatory clinic EHR, or patient-sensor, or other data source, and facilitates accessing data of the source and communicating the data to control server 102 and/or other computing devices on a cloud computing platform, including other remote computers 108.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. In an embodiment, control server 102 includes an adaptive single agent system or an adaptive multi-agent operating system, as described in connection to FIGS. 10A and 10B, but it will be appreciated that control server 102 may take the form of or a non-agent system as well. Embodiments of control server 102 may be a distributed computing system, a centralized computing system, a single computer such as a desktop or laptop computer or a networked computing system. Thus, in some embodiments, control server 102 comprises a multi-agent computer system with software agents, as described in connection to FIGS. 1B, 10A, and 10B.

Figure 1B:
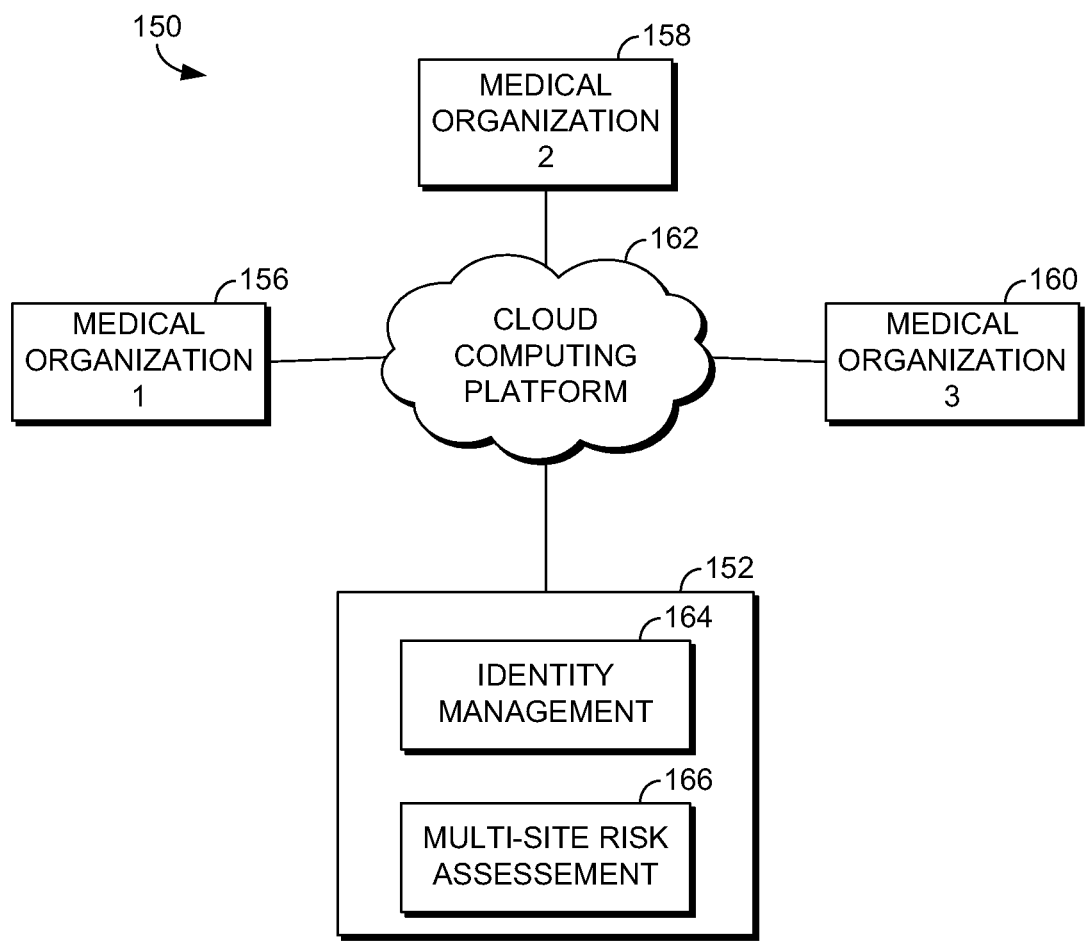
FIG. 1B is a block diagram showing an exemplary architecture for facilitating multi-site clinical decision support in accordance with an embodiment of the present invention.

Turning now to FIG. 1B, another aspect of an operating environment, referred to herein as operating environment 150 is illustrated as a block diagram, in accordance with an embodiment of the present invention, showing an exemplary cloud-computing platform 162 for use by multi-site decision support manager 152. It will be understood and appreciated that the cloud-computing platform 162 shown in FIG. 1B is merely an example of one suitable computing system environment and is not intended to suggest any limitation as to the scope of use or functionality of embodiments of the present invention. For instance, the cloud-computing platform 162 may be a public cloud, a private cloud, or a dedicated cloud. Neither should the cloud-computing platform 162 be interpreted as having any dependency or requirement related to any single component or combination of components illustrated therein. Further, although the various blocks of FIG. 1B are shown with lines for the sake of clarity, in reality, delineating various components is not so clear, and metaphorically, the lines would more accurately be grey and fuzzy. In addition, any number of physical machines, virtual machines, data centers, endpoints, or combinations thereof may be employed to achieve the desired functionality within the scope of embodiments of the present invention. As mentioned, cloud-computing platform 162 comprises a cloud-computing network, which is known in the art as "the cloud."

The cloud-computing platform 162 includes a data center, which may be embodied as data cluster 104, configured to host and support the operation of the manager 152. The manager 152 refers to any software, or portions of software, that run on top of, or access storage locations within, the platform 162. It will be appreciated that cloud-computing platform 162 may include multiple computing devices such as remote computers 108, control servers 102, or computing devices or portions of computing devices. Cloud-computing platform 162 may include virtual machines, such as software, application, operating system, or program that is executed by a processing unit to underlie the functionality of multi-site decision support manager 152. Further, the virtual machines may include processing capacity, storage locations, and other assets to support the multi-site decision support manager 152. In one instance, the computing devices of separate medical organizations, such as medical organizations 206, 208, and 210, host and support the operations of the multi-site data manager, while simultaneously hosting applications.

Figure 10A:
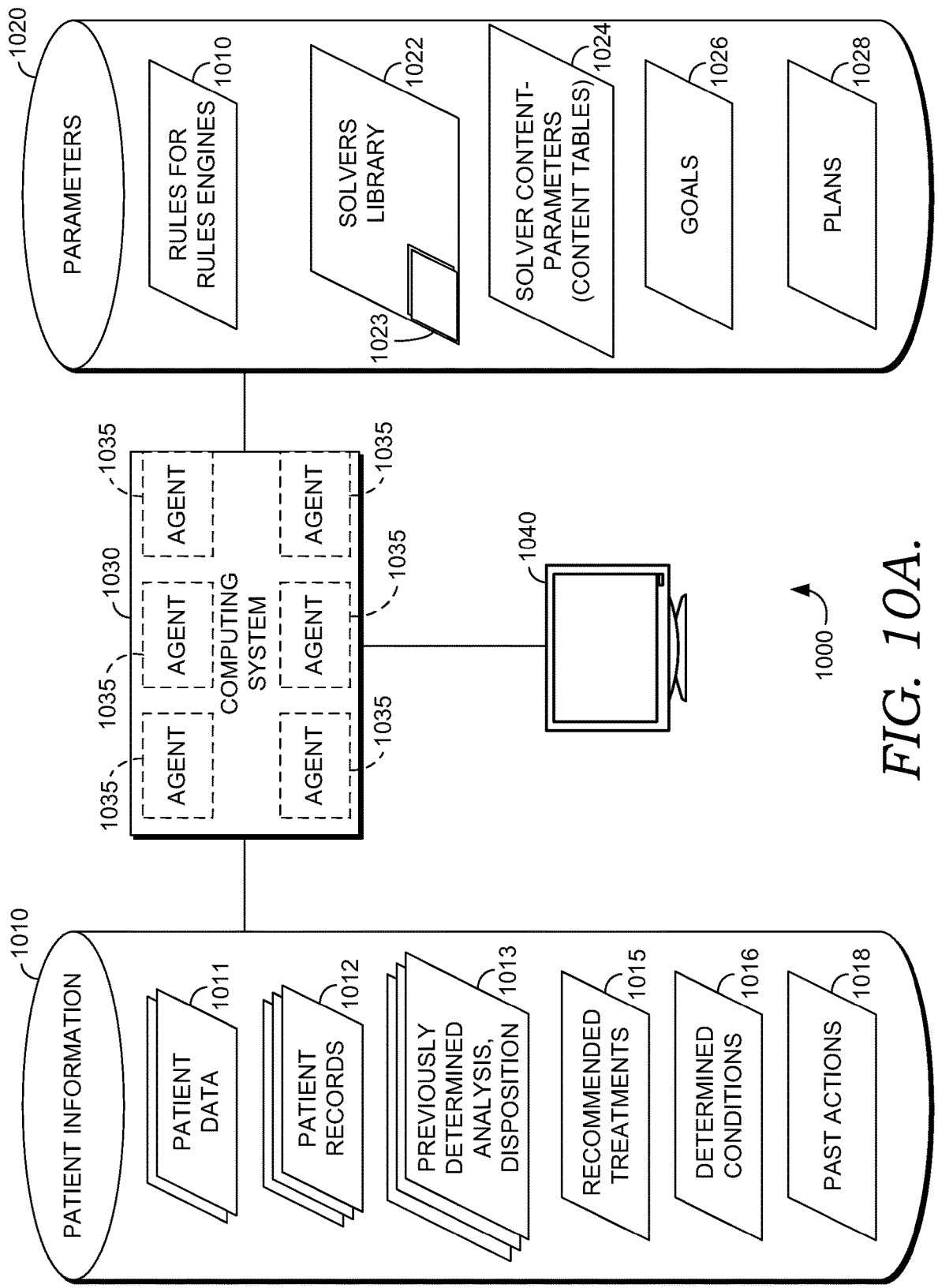
FIG. 10A depicts an aspect of an exemplary framework of a multi-agent computer system suitable for implementing an embodiment of the invention.

Turning briefly to FIG. 10A, in some embodiments, decision support manager 152 and computing platform 162 are implemented in an operating environment 1000 using a multi-agent computer system such as exemplary computer system 1030 with one or more agents 1035, as shown in FIG. 10A and described in greater detail below. But it will be appreciated that computing system 1030 may also take the form of a single agent system or a non-agent system, as described in other embodiments herein. In some embodiments, computing platform 162, which may comprise control server 102 of FIG. 1A, is embodied as computing system 1030, and in some embodiments, decision support manager 152 operates on an embodiment of computing system 1030, which runs on top of, or accesses storage locations within, the platform 162. Computing system 1030 may be embodied as a distributed computing system, a centralized computing system, a single computer such as a desktop or laptop computer or a networked computing system, described in other embodiments herein.

In some embodiments, computer system 1030 is a multi-agent computer system with agents 1035. Multi-agent computer system 1030 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents 1035 based on beliefs, capabilities and choices that communicate via declarative messaging and use abstractions to allow for future adaptations and flexibility. An agent 1035 has its own thread of control which promotes the concept of autonomy.

Embodiments using multi-agent system 1030 provide capabilities to adapt the frequency and messages used for communication between the system 1030 and one or more users through user interface 1040, based on changes to the environment and provide capabilities to filter out noisy data, thereby providing more flexible and adaptable decision-making abilities. In some embodiments, this is accomplished by using leveraging preceptors and effectors. Preceptors or sensors, which in some embodiments may be agents, detect changes in an operating environment and pass this information to the agent system. Effectors, which in some embodiments may be agents 1035, respond directly to changes in an operating environment and consider goals and alternatives prior to implementing a change to the environment.

Embodiments using multi-agent system 1030 further have the capability of supporting intelligent information retrieval and filter out noisy data and utilize heuristics to narrow down a search space to assist in solving complex problems. The multi-agent system 1030 facilitates designing individual agent behaviors and their interactions with other agents 1035 and with users, through user interface 1040. In some embodiments, agents 1035 encoded with both declarative and procedural knowledge and can therefore learn by means of exploration of knowledge and imitation of other agents, for example, by leveraging aggregation of bottom-up and top-down modeling. In some embodiments, the agent system 1030 accepts an abstract workflow and converts it into an actual executable workflow, by for example, using contract and negotiation in multi-agent system 1030. The executable workflow may then leverage agents to run the actual workflow.

Furthermore, embodiments using multi-agent system 1030 coordinate the actions of the agents 1035 to cooperate to achieve common objectives, and negotiate to resolve conflicts, which allows for adaptability, flexibility, and organizational relationships. The transformation of heterogeneous knowledge and content into homogeneous knowledge and content is an important trait of the multi-agent system to provide interoperability. The multi-agent system 1030 operates to achieve its goals while still interacting with agents, including agents outside of the multi-agent system 1030 (not shown here) and users at a higher degree of flexibility.

As a practical example, in some embodiments, a multi-agent system 1030 can be utilized to efficiently process health information from different sources into a standardized data structure where it can be made accessible to various services for consumers, sponsors, and providers as well as for research including virtual clinical trials. Specifically, in an embodiment, multi-agent system 1030 facilitates receiving health information from disparate sources (or crawl disparate sources of health information), such as EHR systems, Health Information Exchanges (HIE)s, claims information, emergency medical records, doctor notes, patient-provided information (such as patient surveys), patient monitors and lab results, or any other source of patient health-related information); indexing the received information, mapping concepts in the received information such as performing synonymic matching and ontology mapping; linking patient records for the same patient; reconciling the health information, and storing it in a "one-record" standardized data structure, where it can be accessible for services and studies. In some embodiments, the various services and studies use information derived from the one record and in some instances generate or (facilitate receiving) new patient health information, which is subsequently crawled (or received) for processing to be incorporated into the one record. Thus, in some embodiments a cyclical process exists. In one such embodiment, provided as an example in FIG. 9, multi-agent system 1030 facilitates monitoring and detecting sepsis in a patient.

In some embodiments, agents 1035 continually monitor events to proactively detect problems and leverage reasoning to react and dynamically alter a plan. Practical reasoning involves managing conflict resolution where the relevant considerations are provided by the agent's desires about what the agent believes. This involves deliberation by deciding what state of affairs the agent wants to achieve using intentions and by means-end reasoning which is how to achieve those desires using plans. By way of background, an intention is stronger than a desire and planning achieves designated goals. Thus in one embodiment, a basic planning module consists of goals and intentions to be achieved, actions that can be performed, and a representation of the environment. These plans can thus handle priorities, uncertainty and rewards to influence the actual plans. An agent has its own thread of control which promotes the concept of autonomy. Additional information about the capabilities and functionality of agents and distributed multi-agent operating systems, as they relate to our invention, is provided in U.S.

patent application Ser. No. 13/250,072, filed on Sep. 30, 2011, which is herein incorporated by reference in its entirety.

Continuing with FIG. 10A, system 1030 is communicatively coupled to patient information 1010 and parameters 1020, and user interface 1040, described below. System 1030 performs processing on patient information 1010 and parameters 1020. In some embodiments, including the practical example described above, system 1030 includes one or more agents 1035, which process patient information 1010 using parameters 1020 to determine goals, plans, patient actions, orders, patient conditions and recommended treatments, or invoke other agents, such as agent solvers, to perform these determinations. In a further example, system 1030 may receive patient data 1011 in the form of a natural language narrative, such as a physician's note, and invoke a data-extraction agent or natural-language extraction agent, from solvers library 1022, to extract discrete data from the note. System 1030 may then use the discrete data and content tables 1024 to instantiate and apply another solver agent (such as a sepsis agent), from solvers library 1022 to determine a patient's condition and recommended treatments. Finally, upon determining a patient's condition and recommended treatments, system 1030 might invoke an expert rules engine using rules 1021 to determine specific actions to take or a disposition for the patient, based on the determined conditions and recommended treatments.

System 1030 is executed by or resides on one or more processors operable to receive instructions and process them accordingly, in one embodiment, and may be embodied as a single computing device, such as computing device 102 or 108 of FIG. 1A, or multiple computing devices communicatively coupled to each other. In one embodiment, processing actions performed by system 1030 are distributed among multiple locations such as a local client and one or more remote servers, or as provided in FIG. 1A as a local server 102 and one or more remote computers 108, or in one embodiment computing devices in cloud platform 162, 152, and at medical organizations 156, 158, and 160 of FIG. 1B. In one embodiment, system 1030 resides on a computer, such as a desktop computer, laptop, tablet, or mobile or smart phone computer. Example embodiments of system 1030 reside on a desktop computer, a cloud computer or distributed computing architecture such as platform 162 of FIG. 1B, a portable computing device such as a laptop, tablet, ultra-mobile P.C., a mobile phone, or a combination of such devices.

Coupled to system 1030 is a display for a user (or user interface) 1040. Display for a user 1040 provides a presentation capability and/or user interface to facilitate communication with users. Using display for a user 1040, a user may view determined results about a patient or provide additional information such as patient information, in one embodiment. Display for a user 1040 may be a single device or a combination of devices and may be stationary or mobile. In some embodiments, a user interface on display device takes the forms of one or more presentation components such as a monitor, computing screen, projection device, or other hardware for displaying output. In some embodiments, a user interface on display device takes the form of one or more presentation components with user input components, such as a remote computer, a desktop computer, laptop, PDA, mobile phone, ultra-mobile PC, computerized physician's clipboard, or similar device. In some embodiments, data elements and other information may be received from display device by a user. Queries may be performed by users through user interface 1040; additional orders, tests, feedback or other information may be provided through the display device to user through user interface 1040. For example, in FIG. 9 an embodiment is described that includes providing an alert (discussed in connection to steps 960 and 970), which in some embodiments may be provided through user interface 1040.

Environment 1000 includes data store 1010 which includes patient information and data store 1020 which includes parameters. In some embodiments, data stores 1010 and 1020 comprise one or more data clusters 104 of FIG. 1A, or networked storage or distributed storage including storage on servers located in the cloud Thus, it is contemplated that for some embodiments, the information stored in data stores 1010 or 1020 is not stored in the same physical location. For example, in one embodiment, one part of data store 1010 includes one or more USB thumb drives or similar portable data storage media. In one embodiment, data stores 1010 and 1020 are distributed at multiple locations including locations of a plurality of medical organizations 206, 208, and 100 or FIG. 2. Additionally, information stored in data stores 1010 and 1020 can be searched, queried or analyzed using system 1030 or user interface 1040, which is further described below.

Data store 1010 comprises information specific to a patient, which in some instances includes incomplete, outdated, uncertain, overlapping, and conflicting information. Moreover, the information might come from a variety of sources and/or exist in a variety of formats including for example, narratives and discretized data. Examples of sources can include patient data from different EHR systems of medical organizations 206, 208 and 100 of FIG. 1B, claims information, traditional hospitals, walk-in clinics, urgent care facilities, other locations that render medical services, as well as in-home patient monitors and patient-wearable sensors or monitors. In one embodiment, patient information includes one or more of patient data 1011, patient records 1012, previously determined analysis or disposition 1013, which are associated with the patient, recommended treatments 1015, previously determined patient conditions 1016, and past actions 1018 performed for the patient. In some embodiments, patient data 1011 can include lab results, real time or near real time information such as data provided by a physician, including information based on observation or a patient's explanation, information provided by a sensor (for example, blood pressure or heart rate), or other patient data. In some embodiments, patient records 1012 can include electronic medical records ("EMR"), health information exchange ("HIE"), personal health record ("PHR"), patient claims, and other health records associated with a patient.

Previously determined analysis and dispositions 1013 include information relating to previous analyses performed on a patient and previous dispositions determined for the patient, including previous analyses and dispositions determined by way of the multi-agent system, in some embodiments. Multiple-agent system 1030 may handle a complex problem, such as determining patient conditions or recommended treatments. Each of the agents 1035 may generate multiple analyses and/or disposition for the patient. For example, as described above, agents operating in parallel and using different input parameters 1020, and in some instances different patient information 1010, may determine a patient's likelihood of having sepsis (or another condition). In some embodiments, a degree of statistical certainty about a determined disposition of analysis may be arrived at by correlating or otherwise comparing each of the separate analyses and/or dispositions. More specifically, if separate agents 1035 each determine substantially the same analysis or disposition using different levels of patient information, then there may be a higher degree of confidence that the analysis or disposition is accurate, given the available patient information. In some embodiments, if the analysis or disposition of the separate agents ends up being a false positive for detection of a condition, then those agents can be designated or otherwise associated as having less effective determination capabilities. Similarly, where agents are more effective (i.e., more accurate and/or more efficient, such as agents able to perform in less time or with less input information) at detecting a patient's condition, then those agents can be designated or otherwise associated as having more effective capabilities. In some embodiments, the most effective agent may be swapped into (or invoked for) the condition detection process. For example, in determining a patient's likelihood of having sepsis, the most effective agent may be invoked. In some embodiments, it is conceivable that performance or effective capability of an agent may be dependent on the specific patient information 1010. For example, in circumstances where a set A of patient information 1010 is available, agent A-prime may have the best performance, but where patient information 1010 is different, such as if a set B of information is available, then agent A-prime is less effective. But another agent, such as agent B-prime, may be more effective. Therefore, an association can be established of which agent is more effective, based on the specific patient information 1010 that is available. In one embodiment, another agent handles this association and invokes the most capable agent based on the available patient information 1010. In another embodiment, this association is encoded as a logic rule or rules engine. In this way, system 1030 learns and also adapts to be more effective, based on the circumstances (such as the available patient information 1010), and in such a manner, the agents may be considered to learn, and are sometimes referred to as learning agents or smart agents. In some embodiments, feedback information is provided to a user or health care provider as to which agent or which patient information 1010 and/or parameters 1020 provide the most accurate determination. This feedback information enables health care providers to streamline care for future patients. For example, if the feedback information indicates that a high probability of detection of a condition, such as sepsis, can be determined based on variables V1 and V2 alone, where the range of variable V1 should be RX-RY for a certain patient type and within a specified time window, and the threshold of variable V2 should be T1, and that variables V3-V5 are unnecessary, then accordingly the health care provider only needs to provide information of variables V1 and V2 and might be able to ignore variables V3-V5. In some embodiments, a health care provider might suggest a set of ranges or thresholds for variables (as parameters 1020) or a range or threshold that is different from what is typically used. After agents using the different ranges of thresholds complete analyses, such as determining likelihood of sepsis, system 1030 can provide information to the health care provider, via user interface 1040, for example, as to whether the suggested ranges or thresholds were more effective or less effective at diagnosing the patient's condition.

Recommended treatments 1015 include currently and previously recommended treatments for a patient. In one embodiment, this information includes time-related or near realtime data associated with the time that the recommended treatment was determined, as well as an indication of whether the recommended treatment has been acted upon. In one embodiment, recommended treatments 1015 also specify how the recommended treatment was determined, including for example, available patient information, the type of solver that was applied, and the resulting patient conditions, thereby enabling a health care provider to query the recommended treatments to see how a particular treatment was determined or to generate a report.

Past actions 1018 include previous actions determined by the multi-agent system 1030. Similarly to what is described above in connection to recommended treatments 1015, past actions 1018 may include time information associated with the time that the action was determined or executed, or may also specify how the action was determined or executed.

Data store 1020 comprises parameters and information associated with the multi-agent system 1030. Although depicted as working with a multi-agent system, in one embodiment, data store 1020 works with single-agent system parameters and information, or non-agent system parameters and information. In one embodiment, data store 1020 includes rules for a rules engine 1021, and solvers library 1022. Rules for a rules engine 1021 include a set of rules or library of rules. In one embodiment, rules 1021 are usable by an expert rules engine, such as an agent 1035 in multi-agent system 1030. Alternatively, in a non-agent embodiment, rules 1021 include a library of rules usable by non-agent processes. One example application of rules 1021 by a rules engine includes determining actions or dispositions associated with a patient from a number of determined conditions or recommended treatments.

Solvers library 1022 includes one or more solvers, which can include non-agent solvers, agent solvers (discussed below) or both. In some embodiments, solvers, which may also be referred to as "resolvers," are applied to determine one or more conditions or recommended treatments for a patient. A finite state machine solver may be used to determine the conditions and recommended treatments of a patient suffering from a number of conditions including sepsis or congestive heart failure, for example. Solvers may also invoke or apply other solvers. Continuing this example, the finite state machine agent solver may invoke a linear solver, such as a mixed integer linear solver, to evaluate each state in order to determine the patient's condition. In one embodiment, the finite state machine returns the actual state for each clinical condition of the patient, which is then passed on to the mixed integer linear solver as parameters, to apply the mixed integer solver based on the clinical state, and content tables 1024. The solvers library 1022 can be updated as new solvers are available. Another example solver is the data-extraction solver, which is described in further detail below. A data-extraction solver is a type of solver that is applied to unprocessed patient information, such as a physician's narrative or patient results data, in order to generate discretized data that is usable for other solvers. For example a natural-language extraction agent may be used to extracts discrete patient-information items from a physicians narrative or patient-provided description.

In some embodiments, agents 1035 facilitate solving problems including the problems described above by employing one or more solvers from solvers library 1022. Furthermore, where existing rule systems may utilize forward chaining, backward chaining and combination, agents 1035 can integrate these rule capabilities as well as other traditional and heuristic techniques. These agents 1035, which may be referred to as agent solvers, can also leverage the best techniques for the problem at hand. They can register their abilities to the overall system and coordinate and communicate with other agents, users, or the overall system, to solve problems based on their current capabilities.

Still further and as described above in the sepsis-detection examples, new or improved solvers, which may be introduced at future times, are able to be leveraged by swapping out current agents with new agents dynamically and without the need to recompile or reconfigure the system. Thus embodiments using multi-agent system 1030 can provide advantages, in some scenarios, over single-agent systems and non-agent systems. By analogy, a single celled organism is analogous to a single-agent system, while a complex multi-celled organism is analogous to the multi-agent system. Accordingly, the "reasoning" capabilities of multi-agent system 1030 are superior to the "reasoning" exhibited by a single-agent system, and the multi-agent system 1030 is not constrained at design time and has the ability to grow and adapt over time based on future needs not anticipated at the time of instantiation or design.

In some embodiments, agents 1035 provide enhanced decision support by using multi-agent properties like collaboration, persistence, mobility and distributed operation, autonomy, adaptability, knowledge and intelligence, reactive and proactive capability, reuse, scalability, reliability, maintainability, security, fault-tolerance, trust, and other primary properties. In addition, numerous secondary properties of multi-agents in embodiments of our invention may facilitate decision support, including: reasoning, planning and learning capabilities; decentralization; conflict resolution; distributed problem solving; divide-and-conquer strategies for handling complex problems; location transparency; allowing for competing objects to be represented; goal-driven or data-driven including agent-to-agent or user-to-agent; time-driven; support for multiple layers of abstraction above services thereby providing flexibility, adaptability, and reuse and simplification; negotiation; hierarchies having dynamic self-organization; abilities to spawn and destroy agents as needed; utilization of transient and persistent data; abilities to address uncertain, missing or inconsistent data; sensitivity to resource and time constraints; ontology-driven functionality; flexible run time invocation and planning; obligations; ability to act to achieve objectives on behalf of individuals and organizations; organizational influence; and other secondary properties. Examples of agents, which may be used by the multi-agent systems of embodiments of our technologies, include: Interface agents; planning agents; information agents; adapter wrapper agents; filter agents; discovery agents; task agents; blackboard agents; learning agents, including supervised learning, unsupervised learning, reinforcement learning, for example; observer agents; inference agents; communication agents; directory agents; administrator and security agents; facilitator agents; mediator agents; and agent solvers. Agent solvers can include, for example: Markov decision processing; approximate linear programming; natural language extraction solvers (such as provided by Discern nCode (Trademark) developed by Cerner Corporation); fuzzy-neural networks, logistic and linear regression; forward-chaining inference (e.g., data-driven); backward-chaining inference (e.g., goal-driven); inductive inference; genetic algorithm; neural network including with genetic algorithm for training; stochastic; self-organizing Kohenen map; Q-learning; quasi-Newton; gradient; decision trees; lower/higher bound search; constrain satisfaction; Naives Bayes fuzzy; LP-solver including mixed integer multi-variable min/max solvers; Finite State Machine and HFSM; temporal difference reasoning; data mining for classification, clustering, learning and prediction; K-means; support vector machines; K-nearest neighbor classification; C5.0; a priori; EM, simulated annealing, Tabu search, multi-criteria decision making, evolutionary algorithm, and other similar solvers.

In some embodiments, where particular types of agent solvers are more efficient at handling certain patient scenarios, a planning agent may invoke the particular type of agent solver most appropriate for the scenario. For example, a finite state machine agent solver and a linear solver agent solver may be invoked by a planning agent, in a scenario involving a patient experiencing congestive heart failure. Similarly, a planning agent might invoke one or more agent solvers for determining likelihood of sepsis, based on patient information 1010 available and/or the effective capability of the agent solver(s). In some embodiments, agent solvers invoke other agent solvers as necessary.

Continuing with FIG. 10A, some embodiments of multi-agent system 1030 employ decision making for applications including, for example, searching, logical inference, pattern matching and decomposition. A subset of solvers library 1022 includes decision-processing solvers 1023. Decision processing solvers 1023 are a special set of solvers used for decision making, although it is contemplated that in some embodiments any solvers of solvers library 1022 or solver agent maybe used for decision processing. Examples of agent decision procession applications include: searching, including heuristic and traditional searching; list; constraint satisfaction; heuristic informed; hill climbing; decision tree; simulated annealing; graph search; A* search; genetic algorithm; evolutionary algorithm; Tabu search; logical inference; fuzzy logic; forward and backward-chaining rules; multi-criteria decision making; procedural; inductive inference; pattern recognition; neural fuzzy network; speech recognition; natural language processing; decomposition; divide-and-conquer; goal tree and subgoal tree; state machine; function decomposition; pattern decomposition; and other decision-processing applications. In some embodiments, agents designed or instantiated with a particular decision-processing application may be swapped out, in a more seamless and transparent manner than with non-agent systems, with another agent having more advanced decision processing functionality as this becomes available or is needed.

Solver content-parameters 1024, which is also referred to as "content tables" 1024, include parameters used for instantiating and applying the solvers. Content tables 1024 provide parameters that specify information regarding conditions, drugs, contra-indications, treatments, orders or other actions, and other parameters used in conjunction with patient information to determine conditions and recommended treatments. In one embodiment, content parameters 1024 are formatted as independent tables, which might take the form of a matrix, which can be maintained, updated, or swapped out with other tables, by health care providers, physicians, or experts independent of patients. For example, a content table may specify parameters relating to diabetes including what factors in patient information indicate that the patient is in hypoglycemia, what factors in patient information indicate that the patient is in hyperglycemia, contra-indications, treatments such as drugs and drug dosages that should be administered, or additional testing that should be ordered. In another example, content tables specify the set(s), range(s), and/or threshold(s) of variables for detecting likelihood of a condition, such as sepsis. In some embodiments, rows of a content table correspond to different sets, ranges, or thresholds of variables such that a first agent can perform its analysis using content specified in a first row A, and a second agent working in parallel (or the first agent at a later time) can perform its analysis using content from a row B. Further, in some embodiments, the results of analyses can be entered into the rows or associated with the rows. Thus, where multiple agents are running analyses in parallel, with each agent using a different set of parameters specified in one row, the results of the row that correspond to the most effective analysis may be provided to the health care provider or otherwise published to the outside world as the result of the determination for whether the patient has the condition, even though in fact there may be multiple separate results from the different analyses, in some embodiments. This is because in many instances, the health care provider only desires to know whether the patient has a particular condition, and doesn't care about a bunch of different agent-generated results coming from diverse parameters 1020, some of which are more accurate and some of which are better than others.

In some embodiments, content tables 1024 and patient information 1010 provide the information necessary for a solver to determine patient conditions and recommended treatments. Content tables may be updated independently, as new information, treatments, or drugs become available.

Goals 1026 include objectives which guide the system, such as embodiments of a multi-agent, single-agent, or non-agent system 1030, in the selection of a plan and, ultimately, the determination of what actions to take place as a result of incoming patient data. Therefore in some embodiments, goals are based on incoming patient information. For example, a goal may specify "determine if patient has sepsis," "manage conditions for sepsis," "manage conditions for sepsis while keeping other patient conditions stable," or "minimize the cost of patient treatment." In some embodiments, goals are used to motivate agents 1035. Specifically, agents 1035 operate under guidance of a goal that is consistent with patient information when deciding what actions to take, plans to select and execute, or which solvers to invoke. Thus, any plan selected and executed will be consistent with the determined goals 1026, which are based on patient information 1010. Moreover, as patient information 1010 changes, such as when newer or additional patient information 1010 becomes available or a patient's condition changes during the course of treatment, goals 1026 may be changed or replaced. In some embodiments such as multi-agent systems operating under the belief-desire-intention ("BDI") model, a goal is analogous to a desire. Accordingly, in one embodiment, agents 1035 may act to fulfill a desire that is based from a set of agent beliefs or facts determined from available patient information 1010. In some embodiments, goals 1026 can be organized in one or more sets, groups, tables, databases, or libraries with, in some embodiments, subgroups related to similar goal-objectives; for example, a subgroup of goals may relate to handling patient treatment costs or treating cancer.

Plans 1028 include, in some embodiments, specific executable algorithms, instructions, schedules, or the similar plans for carrying out a specific objective that is consistent with a determined goal 1026. Alternatively in other embodiments, plans 1028 may specify intention or an intended outcome to be achieved that is consistent with a determined goal 1026. Plans 1228 can include sets or libraries of plans, which in some embodiments are associated with certain goals 1026. For example, for the goal of "manage conditions for sepsis while keeping other patient conditions stable," plans associated with this goal may specify actions for determining a patient's condition by examining patient information including blood pressure and blood oxygen. The plan may further specify recommended treatments, orders, or other plans to be executed. In some embodiments, plans 1028 also include planning agents, which can assist in the selection and execution of a plan. For example, a planning agent may select a plan, which in some embodiments may also be an agent, for treating sepsis based on patient information that indicates sepsis; the plan may specify using solvers such as logistical regression on the patient information to determine the patient's condition and recommended treatment, in one embodiment.

In another example, a specific plan under the sepsis-detection goal, may specify using a data-extraction agent for extracting discrete data items from a physician's note written in natural language, and then instantiating one or more solver agents, which carry out the processes for determining likelihood of sepsis, described herein including the embodiment described in connection to FIG. 9, to determine the patient's conditions and recommended treatments. In one embodiment rather than specifying a specific solver or set of solvers to use (e.g., data-extraction and finite state machine solvers), a plan may specify an intention, (e.g., determine patient's condition when patient information indicates sepsis), and invoke an agent 1035 to select the best solver applicable based on the available patient information 1010. Under the BDI model, a plan is analogous to an intention; thus a plan is sort of like an intention to process the goal with which the plan is associated. The plan 1028 is executed to meet the goal 1026, or partially meet the goal. In one embodiment, a planning engine is used for determining plans 1028 consistent with goals 1026. The planning engine, which could be an agent, non-agent rules engine, a decision tree, or other decision process, selects a plan.

Figure 10B:
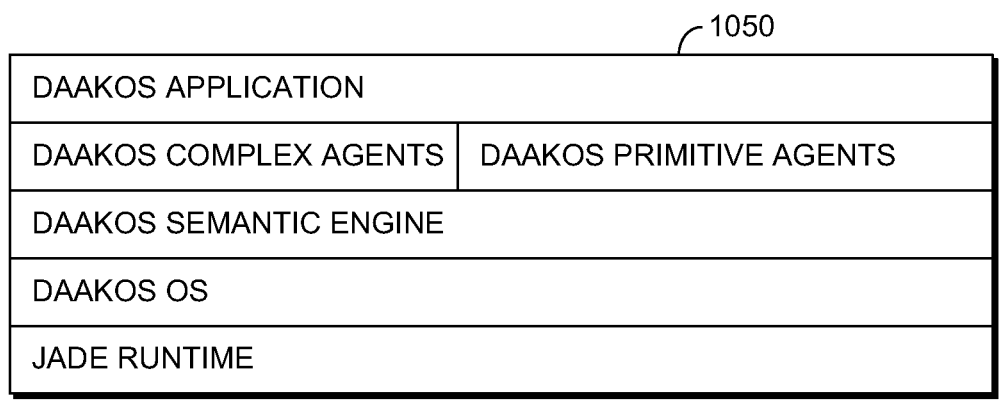
FIG. 10B depicts an aspect of an exemplary framework of a multi-agent system suitable for implementing an embodiment of the invention.

Turning to FIG. 10B, an illustrative example is provided of a framework suitable for implementing a multi-agent system, such as computer system 1030 of FIG. 10A, and is referenced generally by the number 1050. In some embodiments, framework 1050 is suitable for supporting decision support manager 152 of FIG. 1B. In some embodiments, decision support manager 152 is built on framework 1050, and in some embodiments, manager 152's services such as identity management 164 and multi-risk assessment 166 operate as software services on framework 1050. Furthermore, in some embodiments using multi-agent computer system 1030, services 164 and 166 are carried out using one or more agents.

As shown in FIG. 10B, framework 1050 has a layered architecture. At the lowest level depicted in the embodiment shown in FIG. 10B, framework 1050 includes a layer for JADE runtime. In other embodiments, frameworks such as Cougaar, Zeus, FIPA-OS, or an open-agent architecture, may be used. Although not a requirement, it is preferable that the framework include the following properties, which are present in the JADE framework: FIPA compliance; support for autonomous and proactive agents and loosely coupled agents; peer-to-peer communication; fully distributed architecture; efficient transportation of asynchronous messages; support for white and yellow page directory services; agent life-cycle management; agent mobility; subscription mechanism for agents; graphical tools for debugging and maintenance; support for ontology and content languages; library for interaction protocol; extensible kernel for extensions to build customized framework; in-process interface for launching and control; support for running agents on wireless mobile devices; integration with various Web-based technologies; and pure Java implementation.

JADE, which is an acronym for Java Agent DEvelopment framework is a middleware software development framework that is used for facilitating implementation of multi-agent systems. Specifically, the JADE platform includes functionality which facilitates the coordination of multiple agents, and functionality for facilitating the distribution of agent platforms across multiple machines, including machines running different operating systems. Moreover, JADE further includes functionality for changing system configuration at run time by moving agents from one machine to another, as required.

Continuing with FIG. 10B, on top of the JADE runtime framework is the Distributed Adaptive Agent Knowledge Operating System ("DAAKOS"). DAAKOS is a decision-support framework built upon JADE or another multi-agent framework. DAAKOS is a multi-agent framework with heuristic, adaptive, self-optimizing and learning capabilities and the ability to decompose complex problems into manageable tasks to assist clinical decision making at point of care. For example, caregivers and other users can leverage this intelligent agent system to detect a change in personal health or to leverage up to date knowledge about medical conditions, preventive care, and other relevant interests. Accordingly, in one embodiment, DAAKOS can be thought of as an intelligent, self-learning agent system using a cloud metaphor.

Specifically, DAAKOS utilizes multi-agents 1035 that collaborate with each other and interface with external systems, services and users and has the ability to monitor changes and incorporate past knowledge into decision making in order to generate and evaluate alternative plans or adapt plans to handle conflict resolution and critical constraints. A multi-agent virtual operating system provides efficient means to build complex systems composed of autonomous agents with the ability to be reactive, persistent, autonomous, adaptable, mobile, goal-oriented, context aware, cooperative and able to communicate with other agents and non-agents. In some embodiments, intelligence is achieved within agents by way of support provided by a rich ontology within a semantic network. For example, a multi-level of collaborating agents 1035 allows low-level agents to transform data so that it can be passed on to another agent, and to continue the data transformation until the data has been completely transformed from bits of data which may sometimes represent incomplete, outdated, or uncertain data, to form a usable collection of data with rich meaning. In this example, when it becomes necessary to attack complex problems, the agent 1035 is permitted to constrain and narrow its focus at an individual level to support decomposition. Domain specific agents can be leveraged in some embodiments to use an ontology to manage local domain-specific resources.

The DAAKOS operating system layer handles process management, scheduling, memory, resource management, Input/Output ("I/O"), security, planning, as well as other processes traditionally handled by operating systems, and in some embodiments includes memory, which may include short, intermediate, and/or long-term memory, I/O, internal agent blackboard, context switching, kernel, swapper, device resource management, system services, pager, process managers, and logging, auditing, and debugging processes. In some embodiments, the DAAKOS operating system layer is a distributed virtual operating system. On top of the DAAKOS operating system layer, in the embodiment illustratively provided in FIG. 10B, is the DAAKOS Semantic Engine, which provides the platform for DAAKOS agents 1035. DAAKOS agents 1035 include complex agents and primitive agents. On top of the agents' layers are DAAKOS Applications. These include, for example, DAAKOS agent solvers such as a finite state machine instantiated and executed to determine a patient's conditions and recommended treatments, transactions knowledge engines, and other applications leveraging DAAKOS agents 1035.

Now turning back to FIG. 1B, in one aspect, the cloud-computing platform 162 can communicate internally through connections dynamically made between the virtual machines and computing devices and externally through a physical network topology to resources of a remote network such as with medical organizations 156, 158, and 160. By way of example, the connections may include, without limitation, one or more local area networks (LANs) and/or wide area networks (WANs). Such networking environments are commonplace in offices, enterprise-wide computer networks, intranets, and the Internet. Accordingly, the network is not further described herein.

As further shown in FIG. 1B with references to FIGS. 10A and 10B, multi-site decision support manager 152 is capable of communicating with a number of different entities or medical organizations, such as a hospital 156, a physician's office 158, and urgent care clinic 160, for example, for the of patient information collection (sometimes referred to herein as crawling information sources), such as patient information 1010 of FIG. 10A, from a number of individual entities. Patient information 1010 collected from different entities may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information. Additional examples of patient information 1010 is provided in connection to FIG. 10A.

It should be noted that the medical organizations shown as communicating with multi-site decision support manager 152 in FIG. 1B are provided by way of example only and are not intended to limit the scope of the present invention in any way. Each medical organization may have one or more computing devices such as computing device 108 or server 102 of FIG. 1A, for communicating with the decision support manager 152. For example, in some embodiments, a single medical organization has a server 102 with multiple remote computers 108 operating within r associated with the medical organization. It will be appreciated that in some embodiments, each medical organization is an organization for treating patients such as a hospital, urgent care clinic, physician's office, emergency department, and the like. Each medical organization maintains its own enterprise healthcare system and each organization is not directly connected with one another such that separate medical record systems are utilized by each medical organization. The medical organizations send information to the cloud-computing platform 162 and not typically directly between one another. In addition, communication between the manager 152 and the various medical organizations may be via one or more networks, which may comprise one or more wide area networks (WANs) and one or more local area networks (LANs), as well as one or more public networks, such as the Internet, and one or more private networks.

Further, medical organizations may be able to access the manager 152 in a variety of ways within the scope of the present invention. For example, in some embodiments, a medical organization may have a native clinical computing system, which may be able to communicate with the manager 152. In other embodiments, a client application associated with the manager 152 may reside or partially reside on one or more of the medical organization's computing devices facilitating communication with manager 152. In further embodiments, communication may simply be a Web-based communication, using, for example, a Web browser to communicate to the manager 152 via the Internet. Any and all such variations are contemplated to be within the scope of embodiments of the present invention.

In some embodiments, manager 152 is available in the cloud-computing platform 162 in a manner that enables the cross-venue recognition of a patient through the use of a patient identity management component 164 such as an electronic Master Person Index (MPI or EMPI). Patient identity management component 164 allows manager 152 to match data for the same patient that originates with different medical organizations. In some embodiments, identify management component is embodied as one or more software services operating on a multi-agent system 1030, wherein processes associated with patient-record matching are carried out by one or more agents. For example, as further described in connection to FIGS. 8A, 8B, and 8C, in some embodiments management component 164 facilitates record linkage (MPI) functions such as those performed at step 845 in the method provided in FIG. 8A.

Example operating environments 100 and 150 are merely example aspects of a suitable computing environment and are not intended to suggest any limitation as to the scope of use or functionality of the invention. Neither should these environments be interpreted as having any dependency or requirement relating to any single component or combination of components illustrated therein.

Embodiments might be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments might be described in the general context of computer-executable instructions, such as program modules, being executed by a computer. Exemplary program modules comprise routines, programs, objects, components, and data structures that perform particular tasks or implement particular abstract data types. Some embodiments might be practiced in distributed computing environments where tasks are performed by agents 1035 on local or remote processing devices that are communicatively coupled through a communications network. In some embodiments of a distributed computing environment, agents 1035, software routines, or program modules might be located in association with local and/or remote computer storage media (e.g., memory storage devices).

Figure 2:
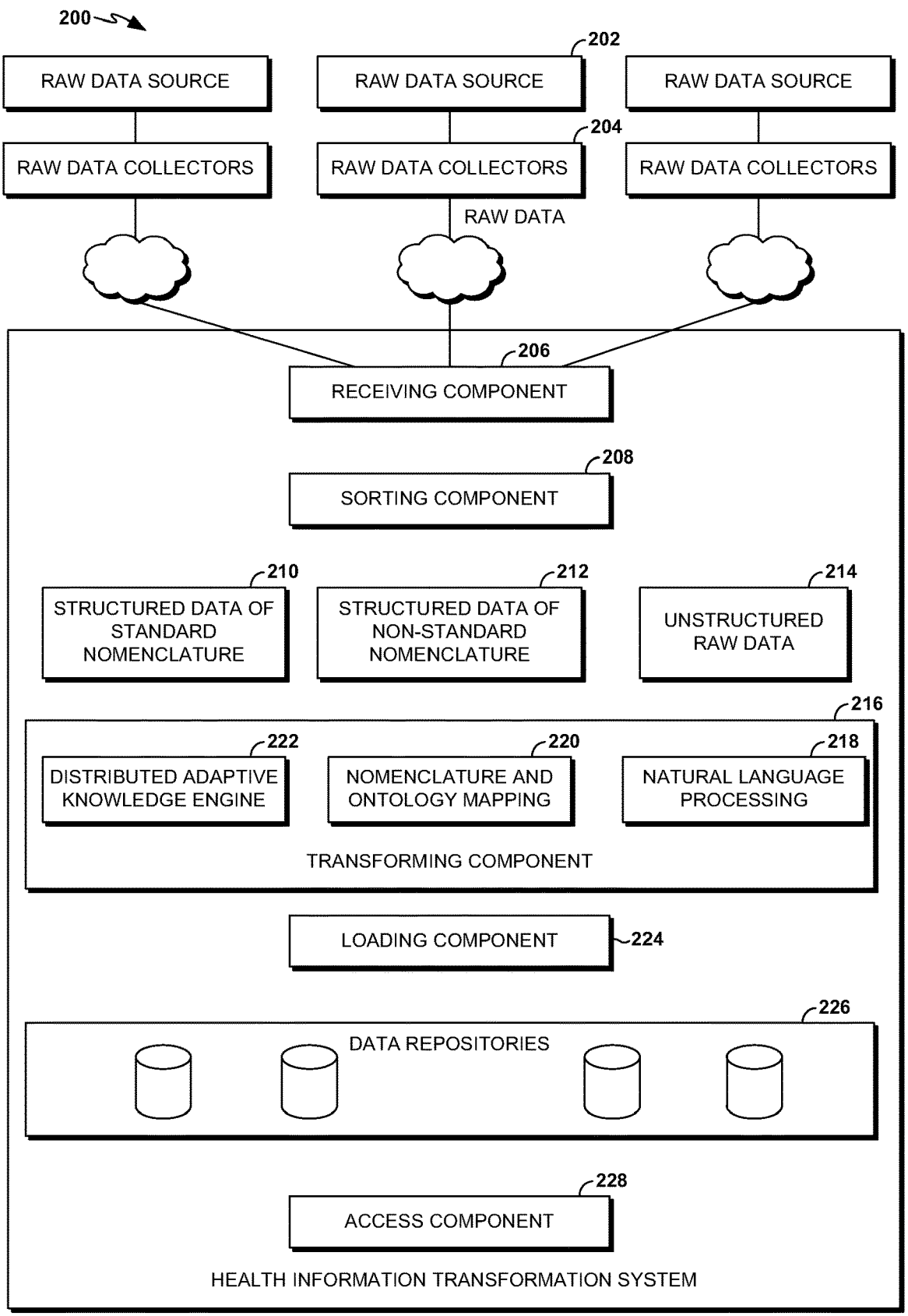
FIG. 2 depicts an exemplary framework of a health information transformation system suitable to implement embodiments of the present invention.

Turning now to FIG. 2, an exemplary framework of a health information transformation system 200 is provided. It will be understood by those of ordinary skill in the art that the arrangement shown in FIG. 2 is merely exemplary. While the health information transformation system is depicted as a single unit, one skilled in the art will appreciate that the health information transformation system is scalable. For example, the health information transformation system may in actuality include a plurality of computing devices in communication with one another. Moreover, the single unit depictions are meant for clarity, not to limit the scope of embodiments in any form.

A receiving component 206 is configured to receive raw data from a plurality of raw data collectors 204, where plurality of raw data collectors 204 is configured to collect raw data from a plurality of raw data sources 202. In one aspect of the invention, raw data sources 202 may comprise electronic medical record sources, images, documents, and medical devices. In turn, electronic medical record sources may comprise electronic clinical documents such as images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. Images may comprise radiographic images, graphs, pictures, photographs, tables, and the like. Likewise, documents may comprise physician notes, physician reports, letters, and such. Finally, medical devices may comprise holter monitors, event monitors, post-event recorders, pre-symptom memory loop recorders, autodetect recorders, implantable loop recorders, glucose monitoring devices, vital signs monitors, and such. Raw data sources 202 may be disparate in nature in that the raw data may be extracted from a variety of different sources as outlined above, and/or from different healthcare facilities and different providers.

Continuing, plurality of raw data collectors 204 may comprise electronic medical records crawlers, clinical and administrative data collectors, claims data collectors, document feed collectors, and medical device feed collectors. In one aspect of the invention, raw data collector 204 collects Health Level Seven (HL7) or Continuity of Care Document (CCD) data. HL7 and CCD develop standards for the electronic exchange of healthcare information and is involved in the sharing of this information. In another aspect of the invention, raw data collector 204 collects Electronic Data Interchange (EDI) data. In one aspect, EDI involves the electronic exchange of standardized information pertaining to insurance claims. EDI data includes uniform data extracted from claims originating from different insurance companies. As well, raw data collector 204 may obtain or collect raw data through e-mail, facsimile, retrieval from the document source, as well as from the medical devices discussed above.

After the raw data is received by receiving component 206, it is sorted by a sorting component 208 into structured data of standard nomenclature 210, structured data of non-standard nomenclature 212, and unstructured raw data 214. Structured data of standard nomenclature 210 may comprise data that is in a computer-useable format suitable for use by a distributed adaptive knowledge engine component 222. For example, data is structured if it is coded with the proper International Classification of Diseases, $9^{th}$ Revision, Clinical Modification (ICD-9-CM) code. In turn, the data has standard nomenclature if it is in a computer-useable language such as Systemized Nomenclature of Medicine (SNOMED) or Logical Observation Identifiers Names and Codes (LOINC). By way of illustrative example, and not by limitation, structured data of standard nomenclature 210 may comprise clinical and administrative data that conforms to the standards set forth by HL7 or other standard-setting bodies, as well as insurance claims information retrieved from EDI.

Continuing, structured data of non-standard nomenclature 212 may comprise data that needs additional processing before it is suitable for processing by distributed adaptive knowledge engine component 222. For example, the data might have the proper ICD-9-CM code but not be in a standard nomenclature, such as, for example SNOMED or LOINC. Structured data of non-standard nomenclature 212 may comprise patient information obtained from an electronic medical records source. By way of illustrative example, a piece of patient-specific raw data extracted from an electronic medical record source may be the term "pityriasis." The term "pityriasis" has the proper ICD-9-CM code of, for example, 696.3, but it is not in standard SNOMED nomenclature. The term "pityriasis" is given standard SNOMED nomenclature (i.e. 77252004). Now the term "pityriasis" can be processed by distributed adaptive knowledge engine component 222. Additionally, unstructured raw data 214 may comprise data obtained from a provider's typed reports, notes, documents and letters. This data is not structured correctly and is not in standard nomenclature. Unstructured raw data 214 needs to be converted from human speech or documentation to a computer-useable language.

A transforming component 216 transforms the sorted data into relevant data through the use of a natural language processing component 218, a nomenclature and ontology mapping component 220, and distributed adaptive knowledge engine component 222. In one embodiment, natural language processing component 218 transforms unstructured raw data 214 into structured data of non-standard nomenclature 212 or structured data of standard nomenclature 210.

As mentioned above, unstructured raw data is converted from human speech or input into a computer-useable language using natural language processing component 218. An exemplary natural language processing system may include Discern nCode™ by Cerner. By way of illustrative example, natural language processing component 218 scans a physician's dictated note and identifies clinical concepts with codified meanings. For example, a physician's note pertains to a patient who has previously been diagnosed with diabetes and is now suffering from diabetic retinopathy. Natural language processing component 218 identifies the clinical concept "diabetic" and the clinical concept "retinopathy." Both of these terms have an established codified (i.e. ICD-9-CM code) meaning. Next, natural language processing component 218 labels the identified clinical concepts as positive, suspected, or negative based on the analysis, understanding, and context of the text within the note. In this case, the clinical concepts "diabetic" and "retinopathy" would both be labeled positive. Natural language processing component 218 then translates the clinical concept into a health concept. Using the example given above, the clinical concept "diabetic" plus "retinopathy" is translated into a health concept "diabetic retinopathy" by applying the correct ICD-9-CM codes and the standard SNOMED nomenclature. The health concept "diabetic retinopathy" is now considered structured data of standard nomenclature 212.

In another aspect, unstructured raw data 214 may be transformed into structured data of non-standard nomenclature. As mentioned above, the unstructured data is transformed into structured data by codifying the data. But the raw data may be given non-standard nomenclature, such as, for example Multum®, instead of standard nomenclature. The non-standard nomenclature may be used if the standard nomenclature is not complete, or does not have the level of detail required with respect to a specific piece of raw data. As well, only non-standard nomenclatures that are already mapped into the system will be utilized.

Nomenclature and ontology mapping component 220 is configured to transform structured data of non-standard nomenclature 212 into structured data of standard nomenclature 210. By way of illustrative example, nomenclature and ontology mapping component 220 receives structured data of non-standard nomenclature 212 comprising a discrete health concept such as "skin eruption" or "rash exanthem" and associates that discrete health concept with a broader health concept such as "eruption of skin." In turn, the broader health concept, "eruption of skin," may be associated with a still broader health concept "rash," where "rash" is structured data of standard nomenclature 210 suitable for processing by distributed adaptive knowledge engine component 222. Still further, nomenclature and ontology mapping component 220 may receive structured data of non-standard nomenclature 212 in the form of related discrete health concepts such as "skin eruption," "comedone," "weal," and "pityriasis" and associate the related discrete health concepts with the broader health concept "eruption of skin." In turn, based on existing relationships within nomenclature and ontology mapping component 220, the broader health concept "eruption of skin" is associated with the health concept "rash", where "rash" is structured data of standard nomenclature 210.

Distributed adaptive knowledge engine component 22 is configured to transform structured data of standard nomenclature 210 into relevant data. In one aspect of the invention, distributed adaptive knowledge engine component 222 may be an artificial intelligence (AI) engine configured to provide decision support concerning which structured data of standard nomenclature 210 should be selected and sent on in the form of relevant data to a loading component 224 for eventual loading into a plurality of data repositories 226. In general terms, distributed adaptive knowledge engine component 222 utilizes multi-agents that collaborate with each other and interface with external systems, services and users and has the ability to monitor changes and incorporate past knowledge into decision making in order to generate and evaluate alternative plans or adapt plans to handle conflict resolution and critical constraints. A multi-agent virtual operating system provides efficient means to build complex systems composed of autonomous agents with the ability to be reactive, persistent, autonomous, adaptable, mobile, goal-oriented, context aware, cooperative and able to communicate with other agents and non-agents. Intelligence is achieved within agents by way of support provided by a rich ontology within a semantic network. For example, a multi-level of collaborating agents allows low level agents to transform data so that it can be passed on to another agent, and to continue the data transformation until the data has been completely transformed from bits of data which may sometimes represent incomplete, outdated, or uncertain data, to a form a usable collection of data with rich meaning. In this example, when it becomes necessary to attack complex problems the agent is permitted to constrain and narrow its focus at an individual level to support decomposition. Domain specific agents can be leveraged in some embodiments to use an ontology to manage local domain specific resources.

Distributed adaptive knowledge engine component 222 handles process management, scheduling, memory, resource management, Input/Output ("I/O"), security, planning, as well as other processes traditionally handled by operating systems, and in some embodiments includes memory, which may include short, intermediate, and/or long term memory, I/O, internal agent blackboard, context switching, kernel, swapper, device resource management, system services, pager, process managers, and logging, auditing, and debugging processes. In some embodiments, distributed adaptive knowledge engine component 222 is a distributed virtual operating system. Distributed adaptive knowledge engine component 222 may also include a Symantec Engine, which provides the platform for complex agents and primitive agents. On top of the agents layers are applications, such as agent solver. Agent solvers may include a finite state machine instantiated and executed to determine a patient's conditions and recommended treatments. Other agent solvers may include searching, including heuristic and traditional searching; list; constraint satisfaction; heuristic informed; hill climbing; decision tree; simulated annealing; graph search; A* search; genetic algorithm; evolutionary algorithm; tabu search; logical inference; fuzzy logic; forward and backward chaining rules; multi-criteria decision making; procedural; inductive inference; pattern recognition; neural fuzzy network; speech recognition; natural language processing; decomposition; divide and conquer; goal tree and sub-goal tree; state machine; function decomposition; pattern decomposition; and other decision processing applications.

As well, distributed adaptive knowledge engine component 222 may perform some interpretation on structured data of standard nomenclature 210, where the interpretation takes place outside the context of a specific patient. By way of illustrative example, and not by limitation, distributed adaptive knowledge engine component 222 may identify structured data of standard nomenclature 210 corresponding to a creatinine value of 2.0 milligrams per deciliter (creatinine is a measure of kidney function), where normal levels of creatinine range from 0.5 milligrams per deciliter to 1.2 milligrams per deciliter. Without looking at the creatinine value in the context of a specific patient, distributed adaptive knowledge engine component 222 determines that the creatinine is elevated and, based on this determination, selects and transforms this piece of structured data of standard nomenclature 210 into relevant data.

Loading component 224 is configured to load the relevant data into a plurality of data repositories 226. In one aspect of the invention, plurality of data repositories 226 may be optimized for specific use cases. By way of illustrative example, at least one data repository of plurality of data repositories 226 may be optimized to store relevant data pertaining to Patient X or Provider Y. The relevant data would comprise all of the relevant data specifically relating to Patient X or Provider Y. A data repository that is optimized for this kind of use is said to be identified and may be suitable for providing in-depth information on Patient X or Provider Y. On the other hand, another data repository of plurality of data repositories 226 may be optimized to store a small subset of relevant data corresponding to a plurality of different patients or providers. A data repository optimized for this kind of use is said to be de-identified and may be suitable, for example, for providing a specific piece of health information on all patients residing within a certain zip code area.

In another aspect of the invention, plurality of data repositories 226 may comprise a master patient index, where a master patient index references all patients known to an area, healthcare facility, organization, enterprise, and the like. In yet another aspect of the invention, plurality of data repositories 226 may comprise at least one of real-time transaction processing data repository, online analytical processing data repository, search index data repository, data mart data repository, and custom data repository. Real-time transaction processing data repository stores relevant data used in real-time transaction processing. These transactions are processed as they occur and are not part of a group of transactions. Further, online analytical processing data repository stores relevant data that can be used to compare relationships between different sets of data. Search index data repository may be used to quickly and accurately locate relevant documents in response to a search query, while data mart data repository stores relevant data used to create decision support. Finally, custom data repository may be customized according to the preferences of a user.

In one aspect of the invention, online analytical processing data repository may be either identified or de-identified. As outlined above, online analytical processing data repository may be identified if it stores relevant data that relates to a specific patient or provider. Alternatively, online analytical processing data repository may be de-identified if it stores relevant data relating to a plurality of patients. In another aspect of system 200, data mart data repository may also be identified or de-identified. In one aspect, relevant data stored in an identified data mart data repository may be used to create decision support for a patient as outlined further below.

An access component 228 is configured to provide access to plurality of data repositories 226. In one aspect of the invention, access component 228 may provide access to healthcare applications and services comprising at least one of eVisit, care card, condition management, evaluation and management (E/M) coding, quality reporting, and search applications. Still further, in another aspect, access component 228 may provide a provider care card application and a patient care card application access to data mart data repository. These two applications use the relevant data stored in data mart data repository to create graphical user interfaces in the form of provider care cards and patient care cards. Provider care cards have a number of different capabilities that assist providers in caring for their patients, while patient care cards are designed to help patients assume a more active role in managing their health.

As mentioned above, relevant data stored in data mart data repository may be used to create decision support for a patient. The provider/patient care card application, in one example, may utilize a typical rules engine to create decision support for the care card application. The rules engine may determine actions or dispositions with respect to a patient by applying a set of pre-defined rules to a pre-determined number of conditions or treatments. In another aspect, the provider/patient care card application may utilize an artificial intelligence (AI) engine, such as, for example, distributed adaptive knowledge engine component 222, that uses relevant data stored in an identified data mart data repository to provide flexible, adaptive, decision support for a patient. For example, the AI engine in the care card application may use the relevant data along with a set of parameters that specify information about drugs, contra-indications, diagnoses, conditions, and the like to instantiate and apply a program to determine recommended treatments for a patient. This process takes place in the context of a specific patient unlike both the rules engine mentioned above. By way of illustrative example, and not by limitation, the AI engine in the care card application identifies relevant data stored in data mart data repository corresponding to a creatinine level of 2.0 milligrams per deciliter for Patient X. A typical rules engine would automatically generate an alert to a provider based on the elevated level. But distributed adaptive knowledge engine component looks at the creatinine level in the context of Patient X. Patient X, for example, has end-stage renal disease and will always have an elevated creatinine level. Distributed adaptive knowledge engine component processes all of the relevant data relating to Patient X and determines that while the creatinine level is elevated in general, an alert does not need to be provided because the creatinine level is within normal range for Patient X.

Figure 3:
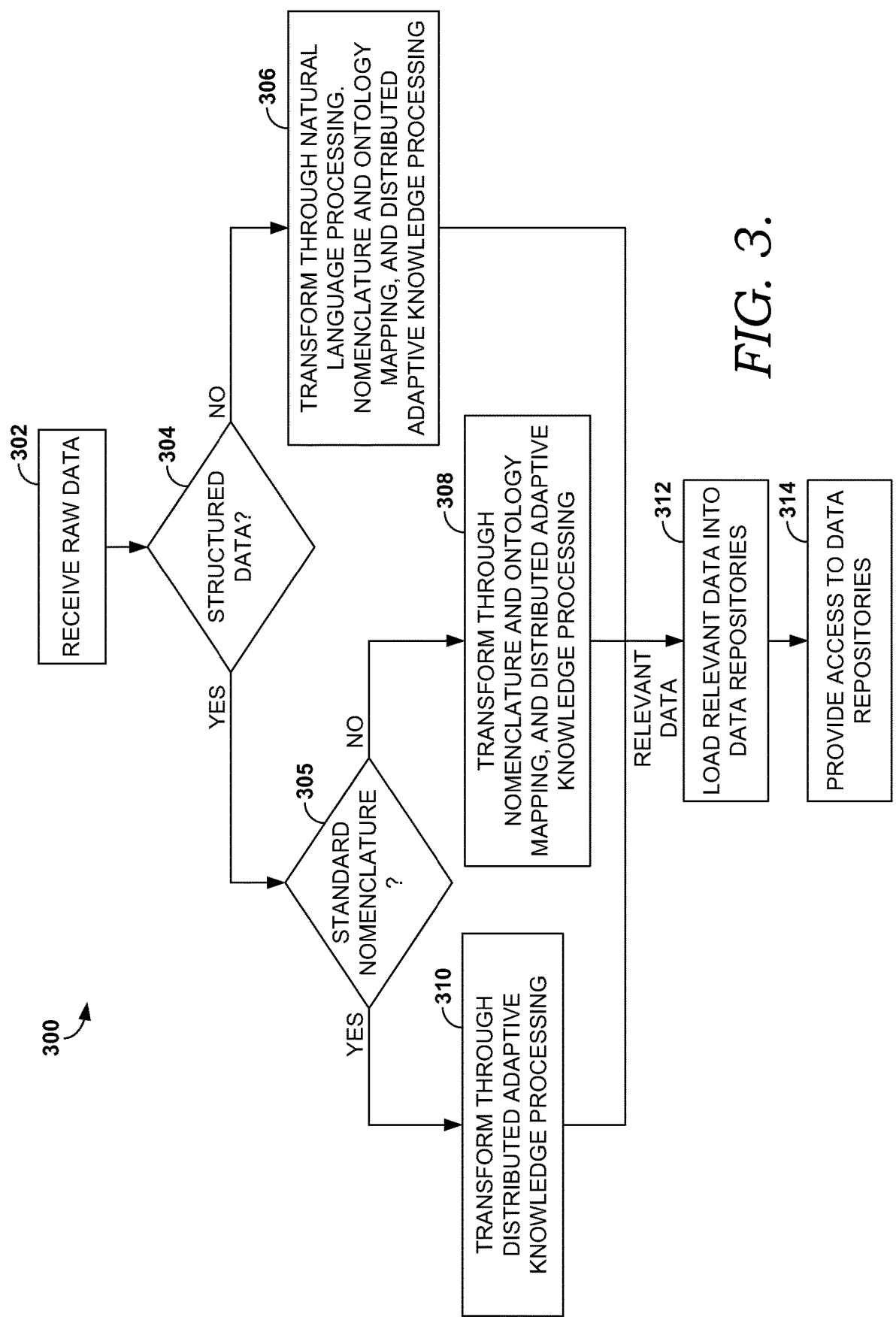
FIG. 3 depicts a flow diagram of a method to transform health information in accordance with an embodiment of the present invention.

Turning now to FIG. 3, a flow diagram of a method 300 to transform raw healthcare data into relevant healthcare data is provided. The information outlined above with respect to FIG. 2 is also applicable to method 300. At step 302, raw data is received from a plurality of data collectors, where the plurality of data collectors extract raw data from a plurality of data sources. At step 304 the raw data is sorted by making a determination as to whether the raw data is structured. If the raw data is structured, a determination is made at step 305 as to whether the structured data has standard nomenclature or non-standard nomenclature. If the raw data is structured and has standard nomenclature it is transformed at step 310 into relevant data through distributed adaptive knowledge processing. If it is determined at step 305 that the raw data is structured but does not have standard nomenclature, it is transformed at step 308 into relevant data through nomenclature and ontology mapping, and distributed adaptive knowledge processing. Returning to step 304, if it is determined that the raw data is not structured data, the raw data is transformed into relevant data at step 306 through natural language processing, nomenclature and ontology mapping, and distributed adaptive knowledge processing. At step 312, the relevant data is loaded into a plurality of data repositories, and at step 314 access to the plurality of data repositories is provided.

Provider Care Cards

Figure 4:
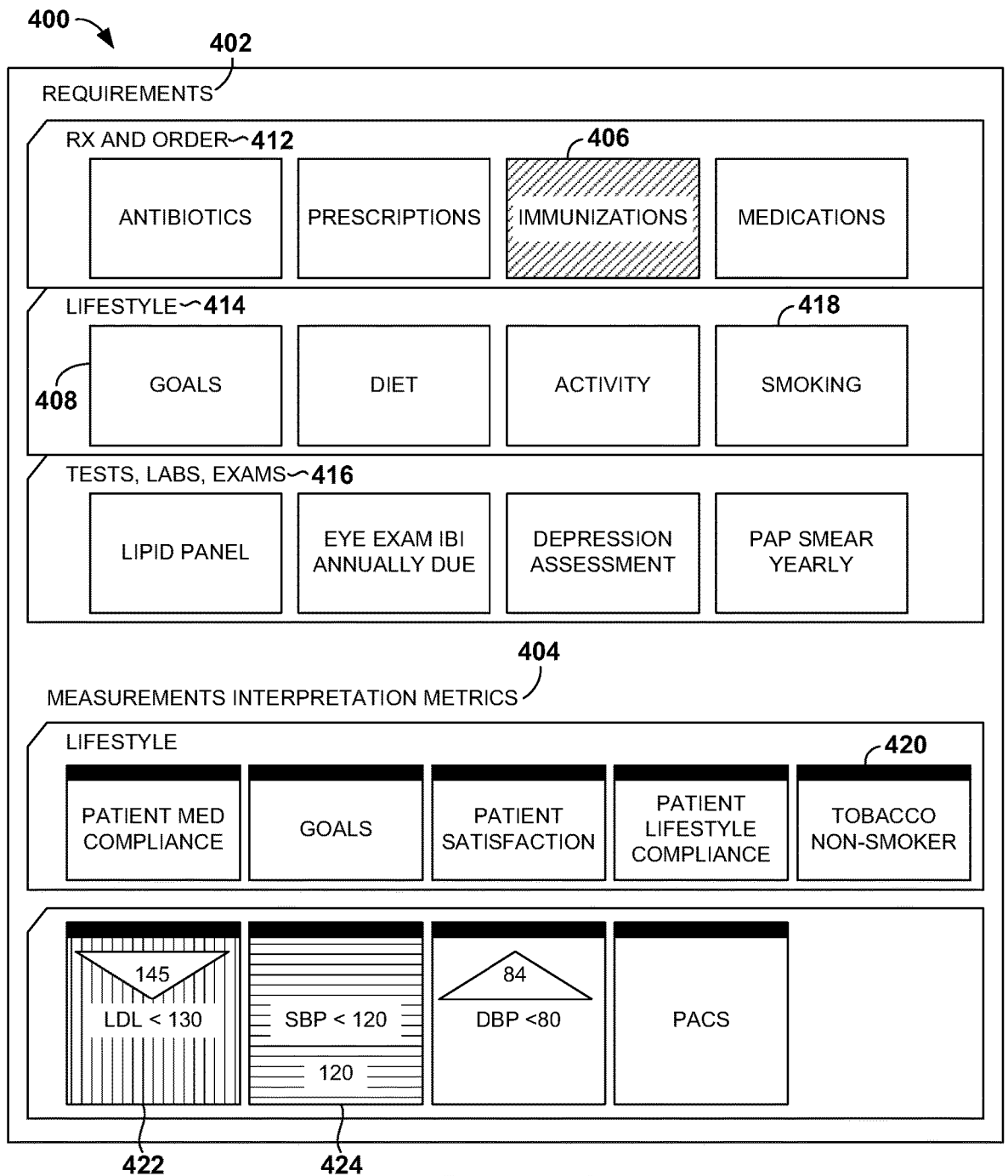

Turning now to FIG. 4, an exemplary graphical user interface (GUI) 400 of a provider care card is shown. As mentioned above, provider care cards are built upon relevant healthcare data generated by the health information transformation system. These easy-to-use, flexible, adaptive care cards allow providers to more effectively care for their patients by providing them with a comprehensive view of their patient's health. In one aspect of the invention, GUI 400 comprises a requirements display area 402 configured to display at least one or more clinical measures 418 relating to at least one patient, and a measurements display area 404 configured to display at least one or more measurements 420 completed for one or more clinical measures 418 relating to at least one patient. As well, GUI 400 comprises a first plurality of microdisplays 406 configured to display a first visual indicator for each of the clinical measures that have been met, and a second plurality of microdisplays 408 configured to display a second visual indicator for each of the clinical measures that have not been met. For example, immunization 406 has been met and not smoking 418 has not been met. Clinical measures 418 may comprise any health-related concept that is used by a provider in the care of a patient. Examples include prescriptions, lifestyle, diet, activity, diseases, conditions, mental health, over-the-counter medications, homeopathic medications, herbal remedies, allergies, family support, age, and many more. Clinical measure 418 is considered met if the patient or provider has acted with respect to clinical measure 418. For example, a clinical measure relating to a lipid panel would be met if the patient or provider drew a sample of the patient's blood and obtained a lipid panel.

In one aspect of the invention, requirements display area 402 may comprise at least an Order and Prescription area 412, a Lifestyle area 414, and a Tests, Labs, and Exams area 416. Order and Prescription area 412 may have an antibiotics area that contains information, for example, on which antibiotics a patient is taking, or which antibiotics a patient is allergic to, a prescription area containing information, for example, on which prescriptions the patient is currently taking, a medication area that documents all over-the-counter medications the patient is taking, and an immunization area that may contain information on the current immunization status of the patient.

Lifestyle area 414 may comprise a goals area containing information on provider goals for a patient. Provider goals may include general goals, specific goals, long-range goals, or short-range goals for patient care. By way of illustrative example, a provider may have a bed-ridden patient suffering from obesity, high blood pressure, and pressure sores. The provider's goals for this patient may include general, long-range goals such as having the patient lose weight and begin walking within the next three months, and specific, short-term goals such as having a home health nurse visit the patient and provide wound care for the pressure sores within the next week. Lifestyle area 414 may also comprise a diet area relating to dietary goals and restrictions for the patient, an activity area containing information on, for example, current activity and desired activity, and a smoking area containing information about the patient's tobacco history. Still further, Tests, Labs, and Exams area 416 may comprise such information as a lipid panel, depression assessment, blood pressure screening, eye exam, foot exam, pap smear, blood metabolic panel, thyroid panel, and the like.

In another aspect of the invention, requirements display area 402 may be customized to at least one or more conditions of the patient. A condition may be defined as the presence of illness, disease, or a state not normally present in the patient such as pregnancy. By way of illustrative example, and not by limitation, a patient suffering from cancer may have a cancer area within the requirements display area 402. The cancer area may contain clinical measures 418 specific to that condition such as a clinical measure 418 on how much radiation the patient has received in the course of her cancer treatment, or a clinical measure 418 concerning clinical studies in which the patient is enrolled.

As mentioned above, measurements display area 404 is configured to display one or more measurements 420 completed for one or more clinical measures 418 relating to a patient. Measurements 420 may comprise patient compliance, cost of care, patient satisfaction, patient lifestyle compliance, patient goal compliance, results of blood work or procedures, blood pressure readings, potentially avoidable complications (PAC), and the like. PACs may be defined as non-typical services associated with the care of a patient with a chronic condition. For example, diabetic patients typically have circulatory problems and neurological problems especially with respect to their feet. A typical service for a patient that is being followed for diabetes is a regular foot exam. A PAC associated with diabetes would be wound care for a diabetic patient with a foot ulcer who was not receiving regular foot exams.

In one aspect of the invention, measurement display area 404 may be configured to display measurements trends for at least one or more of measurements 420. Measurement trends for measurements 420 may be shown, for example, by an arrow, graph, table, chart, and such. This is useful, for example, when a provider is following the blood glucose levels of a diabetic patient. As well, measurement display area 404 may be configured to receive at least one or more measurements 420 from the patient. Measurements 420 may be electronically sent by the patient, received via a telephone call from the patient and inputted by the provider or someone from her staff, and the like.

Measurement display area 404 may also be configured to display comparisons between at least one or more measurements 420 of the patient and measurements 420 of a comparison group. The comparison may be at least one of condition-based, outcome-based, demographic-based, financial-based, geographic-based, and such. By way of illustrative example, a provider may be interested in comparing the cost of care for Patient X who has diabetes. The provider could access a condition-based and financial-based comparison of patient X and a comparison group. The comparison group could comprise other diabetic patients seen by the provider, diabetics within a certain zip code, diabetic patients from the population at large, and so on. The use of comparisons gives the provider important feedback regarding the quality of care the provider is delivering to her patient.

Continuing on, measurement display area 404 may be configured to display a third visual indicator 422 if measurement 420 is abnormal and a fourth visual indicator 424 if measurement 420 is normal. For example, third visual indicator 422 indicates that the patient has an abnormal LDL, and fourth visual indicator 424 indicates that the patient's systolic blood pressure is normal. By way of illustrative example, and not by limitation, third visual indicator 422 may be colored red to alert the provider that measurement 420 is abnormal. Additionally, fourth visual indicator 424 may be colored green to alert the provider that measurement 420 is within normal range. In one aspect of the invention, an alert, notification, or questionnaire may be automatically sent to the patient if measurement 420 is abnormal as shown by third visual indicator 422. The alert, notification or questionnaire may be sent via email, text message, automated phone call, and such. By way of illustrative example, and not by limitation, a diabetic patient may be responsible for monitoring his blood glucose levels at home and sending them to the provider. If the blood glucose levels are outside the normal range, a questionnaire may be automatically sent to the patient through electronic mail asking the patient what his symptoms are and requesting that a repeat blood glucose level be drawn and the results sent to the provider.

In one aspect of GUI 400, first plurality of microdisplays 406 are shaded a first color to indicate clinical measure 418 has been met, and second plurality of microdisplays 408 are shaded a second color to indicate clinical measure 418 has not been met. But it should be understood that any number of visual indicators may be used to indicate whether the clinical measure has been met/not met including words, symbols, patterns, and the like.

Additionally, at least one of second plurality of microdisplays 408 may be actionable meaning that a provider can click on the microdisplay 408 and initiate at least one of an ordering conversation, a quality measure conversation, a data review conversation, a document conversation, a scheduling conversation, a billing conversation, or a communication conversation. Upon clicking at least one of second plurality of microdisplays 408, the provider may be taken to computer interface that allows the provider, for example, to retrieve or view a document associated with the patient, order a test, procedure, or service for the patient, schedule the patient for a visit with the provider, retrieve quality measures, or initiate a communication with the patient through the use of, for example, electronic mail, text messaging, and the like. Using the example set out above concerning the patient suffering from obesity, hypertension, and pressure sores, an order conversation may comprise the provider ordering a home health nurse to visit the patient since the patient is bed-ridden in his home, while a document conversation may comprise the provider retrieving a consult letter from a bariatric physician who recently saw the patient. In addition, a communication conversation may comprise the provider sending an electronic message to the patient inquiring as to the status of the patient's pressure sores.

In another aspect of the invention, first plurality of microdisplays 406 may have mouse hover capabilities allowing the provider to hover over at least one of first plurality of microdisplays 406 and view information concerning that microdisplay. Such information may comprise lab results, examination results, procedure results, evaluation reports, and the like. Additionally, first plurality of microdisplays 406 and second plurality of microdisplays 408 may be organized into patient responsible tasks and provider responsible tasks. By way of illustrative example, and not by limitation, a patient responsible task may be to monitor blood pressure readings at home. The patient would be responsible for taking the blood pressure reading and communicating this reading to the provider through electronic mail, text messaging, a telephone call, and the like. Likewise, a provider responsible task in the above example, may comprise ordering a prescription for antihypertensive medication if the blood pressure readings are above a certain level. The provider could accomplish this task, for example, by initiating an ordering conversation through second plurality of microdisplays 408.

FIG. 5 represents another exemplary graphical user interface (GUI) 500 of a provider care card in accordance with an aspect of the present invention. GUI 500 comprises a requirements display area 502 configured to display at least one or more clinical measures 518 relating to at least one patient. Requirements display area 502 corresponds, for example, to requirements display area 402 of FIG. 4. As well, GUI 500 comprises a measurements display area 504 configured to display one or more measurements 520 completed for one or more clinical measures 518 relating to at least one patient. Continuing, GUI 500 has a first plurality of microdisplays 506 configured to display a first visual indicator for each of the clinical measures 518 that have been met. First plurality of microdisplays 506 correspond generally, for example, to first plurality of microdisplays 406 of FIG. 4. Finally, GUI 500 comprises a second plurality of microdisplays 508 configured to display a second visual indicator for each of the clinical measures 518 that have not been met. Second plurality of microdisplays 508 corresponds, for example, to second plurality of microdisplays 408 of FIG. 4.

Figure 6:
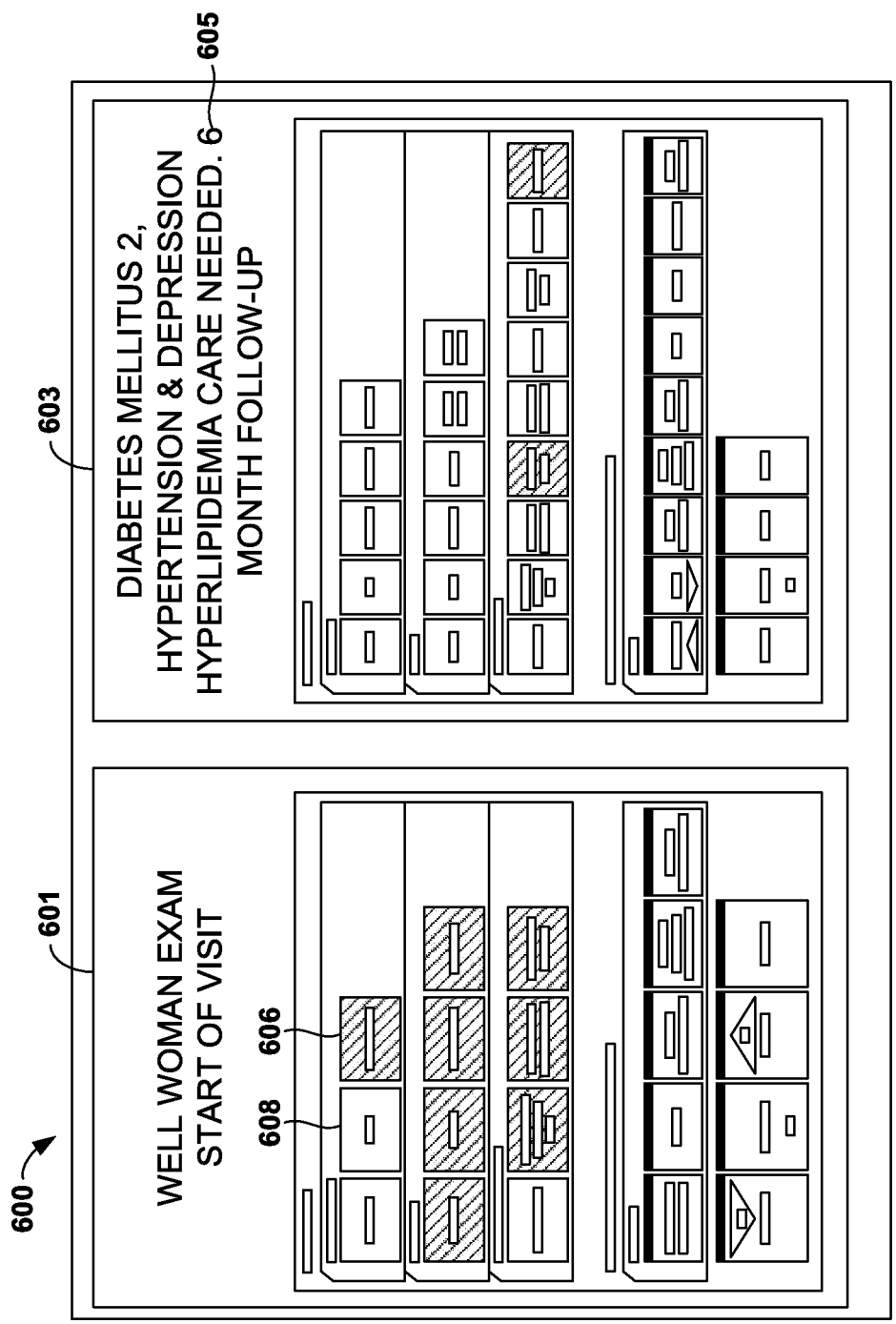

Turning now to FIG. 6, another exemplary graphical user interface 600 of a physician care card in accordance with an aspect of the present invention is shown. In one aspect, GUI 600 is configured to display at least one or more conditions 605 of the patient allowing a provider a comprehensive view of her patient's health. In yet another aspect of the invention, GUI 600 may be configured to allow the provider to select one or more condition-centric views for the patient. For example, a provider may have a patient with multiple conditions, but the provider wishes to focus on the condition that is the reason for the patient's present office visit to the provider. The provider may limit the display of GUI 600 to the condition at issue.

In addition, GUI 600 is configured to display a first plurality of microdisplays 606 and a second set of microdisplays 608 corresponding to first plurality of microdisplays 406 and second plurality of microdisplays 408 of FIG. 4. First plurality of microdisplays 606 and second plurality of microdisplays 608 may be arranged over a time period ranging from at least an initial point of provider/patient contact 601 to at least a current point of provider/patient contact 603 regardless of whether a clinical measure has been met. This view allows the provider to see how well he or she is doing in meeting clinical measures relating to the patient. For example, the provider would likely be delivering quality healthcare if the majority of visual indicators indicate that clinical measures have been met for the patient. Alternatively, if the majority of visual indicators indicate that the clinical measures have not been met for the patient, the provider could use this information to improve her practice. In addition, if there are patient responsible tasks, the provider would be able to see how well the patient is doing in taking responsibility for her own health care by checking to see if the visual indicators associated with the patient responsible tasks indicate that the clinical measures have been met.

Patient Care Cards

Turning now to FIG. 7, an exemplary graphical user interface (GUI) 700 of a patient care card in accordance with an embodiment of the present invention is provided. As mentioned above, patient care cards are built upon the relevant healthcare data that is generated through the health information transformation system. The patient care card is a user-friendly GUI that helps patients assume a more active role in managing their health.

In one aspect, GUI 700 comprises a requirements display area 702 that is configured to display at least one or more clinical measures 718 relating to a patient. Also, GUI 700 comprises a visual indicator 708 that changes depending on whether the at least one or more clinical measures 718 has been met or not met. Clinical measures 718 may comprise any healthcare-related concept that is used in patient care. Clinical measure 718 is met if a patient has acted with respect to clinical measure 718. For example, clinical measure 718 for a diabetic patient may include blood glucose levels. Clinical measure 718 is met if the patient takes a blood glucose reading and inputs it into GUI 700. Additionally, visual indicator 708 comprises any number of indicators such as, for example, color-coding, symbols, words, shading, and such. In one aspect, visual indicator 708 may be shaded a first color to indicate clinical measure 718 has been met, or visual indicator 708 may be shaded a second color to indicate that clinical measure 718 has not been met.

GUI 700 may be configured to display at least one or more conditions of the patient. And, further, the displayed clinical measures 718 may be customized to the at least one or more conditions of the patient. Thus, for example, a patient care card for a patient suffering from depression and diabetes may display clinical measures 718 related to both of these conditions such as blood glucose levels, a depression symptom checklist, and an exercise log.

In another aspect, GUI 700 comprises a requirements display area 702 configured to display at least one or more clinical measures 718 relating to a patient, a measurements display area 704 configured to display one or more measurements 720 completed for one or more clinical measures 718 relating to the patient, a visual indicator 708 that changes depending on whether the at least one or more clinical measures 718 has been met, and a trend display area 710 configured to display at least one or more graphical representations of clinical measures 718 relating to the patient. Measurements 720 may comprise results of blood work or procedures, blood pressure readings, blood glucose levels, exercise logs, completed symptom checklists, weight readings, and the like. In turn, graphical representations associated with trend display area 710 may include bar graphs, scatter plots, pie charts, pictographs, line graphs, histograms, and the like.

In one aspect, measurement display area 704 may be configured to display a first indicator if measurement 720 is abnormal, and a second indicator if measurement 720 is within normal limits. First and second indicators may include visual indicators such as color, shading, and words, and auditory indicators such as alarms, chimes, rings, and such. If measurement 720 is abnormal, a health alert display area 714 may be configured to display a message. In one aspect, the message may be sent by the patient's provider in response to the receipt of abnormal measurement 720. In another aspect, the message may be automatically generated upon detection of abnormal measurement 720.

In another aspect, measurements display area 704 may be configured to display comparisons between measurement 720 of the patient and measurement 720 of a comparison group. The comparison may be at least one of condition-based, demographic-based, cost-based, or geographic-based. The use of comparisons allows the patient, for example, to determine if the care she is receiving from her provider is not only cost-efficient, but also effective.

Continuing on, GUI 700 may be configured to be actionable. In one aspect, the action comprises a communication conversation with a provider, or a scheduling conversation with a provider. For example, Patient X may be concerned with measurement 720. Patient X is able to click on measurement 720 to access a communication screen. Patient X then inputs his message, and the message is electronically sent to the patient's provider. Or Patient X may wish to schedule an appointment with his provider; Patient X may access a scheduling screen and schedule the appointment. As well, GUI 700 may be configured to have hover capabilities allowing the patient to hover over one or more clinical measures 718 or measurements 720 and view healthcare information related to the one or more clinical measures 718 or measurements 720. By way of illustrative example, and not by limitation, Patient X would like to have more information about clinical measure 718 relating to weight. Patient X could hover over clinical measure 718 dealing with weight and access informational material on weight.

In another aspect, GUI 700 is configured to receive documentation, scheduling information, messages, measurements, or orders relating to at least one or more clinical measures 718 from at least one or more providers. Thus, if a patient recently had blood drawn at her provider's office, the provider could electronically send the results to the patient obviating the need for a phone call. If the blood work is abnormal, a message may be sent along with the results and displayed in health alert display area 714. The message would alert the patient and request that she contact the provider. In one aspect, a provider may send a post-treatment survey to the patient. The feedback provided by the survey furthers the goal of improving the quality of healthcare delivered by the provider.

In yet another aspect, GUI 700 comprises a requirements display area 702 configured to display at least one or more clinical measures 718 relating to a patient, and a measurements display area 704 configured to display one or more measurements 720 relating to the patient. As well, GUI 700 comprises a first visual indicator 708 that changes depending on whether the at least one or more clinical measures 718 has been met, a trend display area 710 configured to display at least one or more graphical representations of the clinical measures 718 relating to the patient, and a patient input display area 712 configured to receive inputs from the patient, where the inputs correspond to at least one or more of clinical measures 718 relating to the patient. Patient input display area 712 may be configured to receive inputs from the patient regarding whether to save measurement 720, change a value associated with clinical measure 718 (such as setting a new weight goal), or delete measurement 720 or clinical measure 718.

GUI 700 may also be configured to display a control panel, where the control panel comprises at least one of a to-do list, a settings panel, or a dashboard panel. The dashboard panel may be configured to allow the patient access to a variety of suitable healthcare-related applications.

Figure 8A:
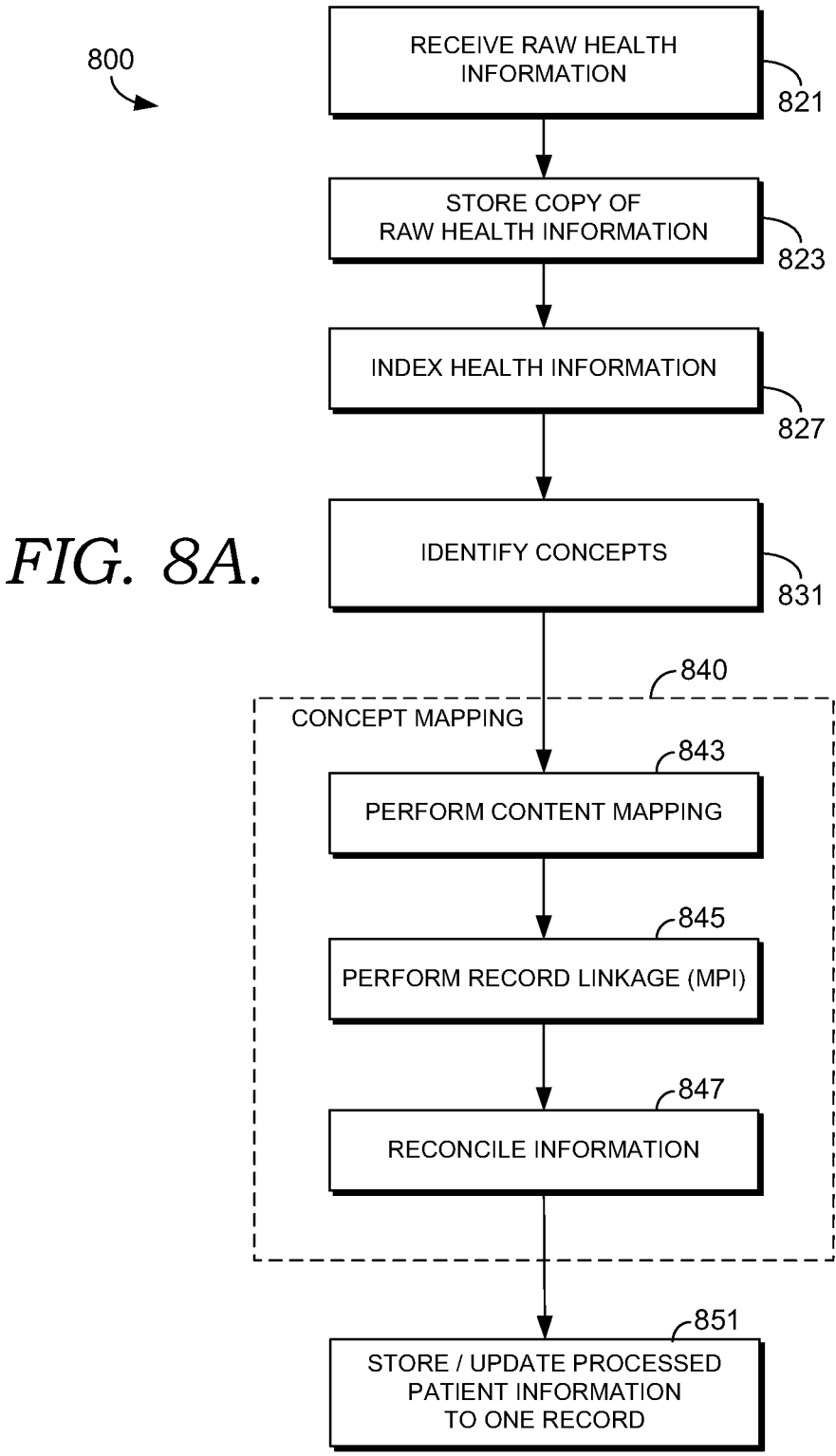
FIG. 8A depicts a flow diagram of a method for generating a standardized patient record, in accordance with embodiments of the invention.
Figure 8B:
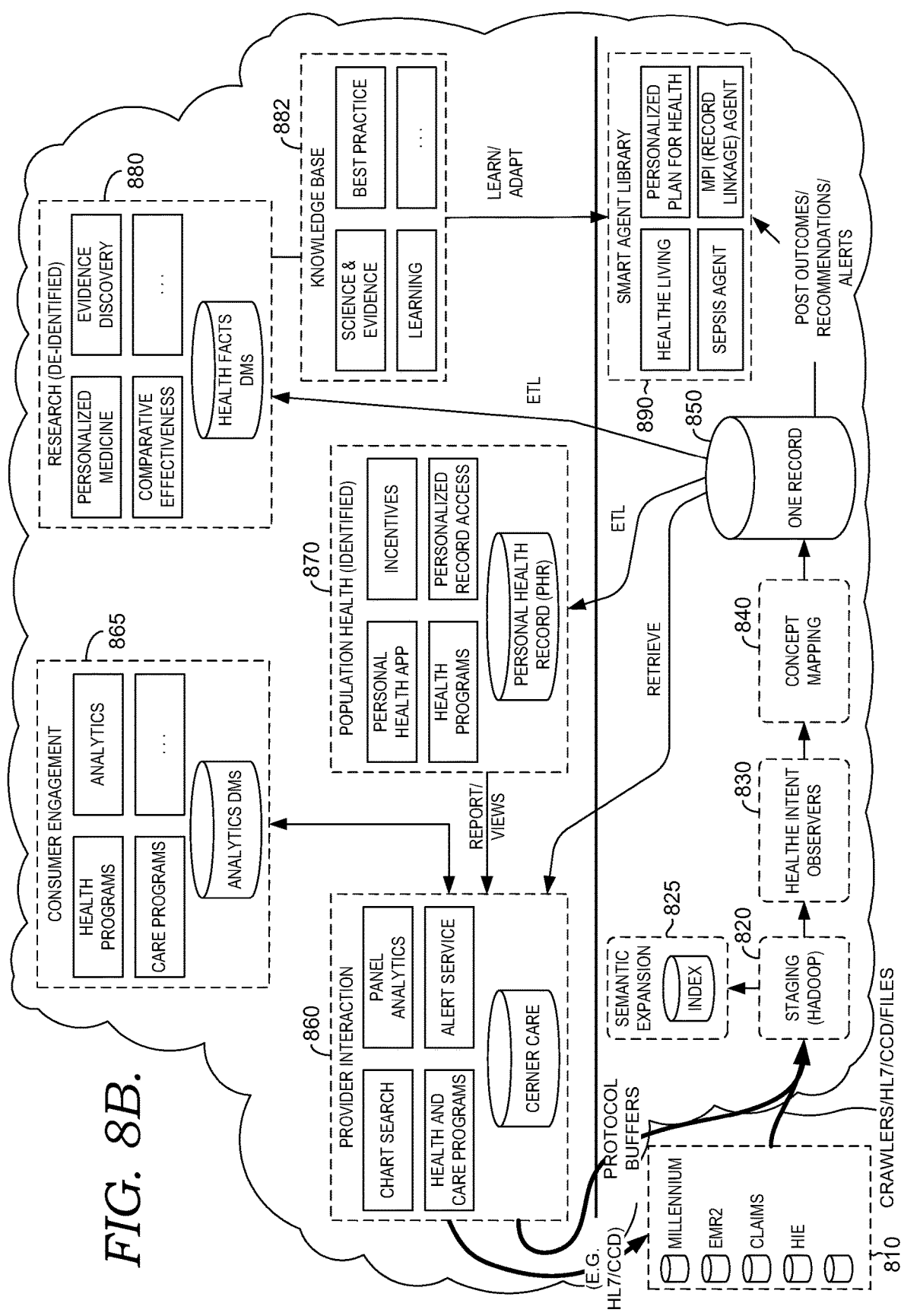
FIGS. 8B and 8C depict illustrative example embodiments of systems and methods for transforming health information in accordance with embodiments of the invention.
Figure 8C:
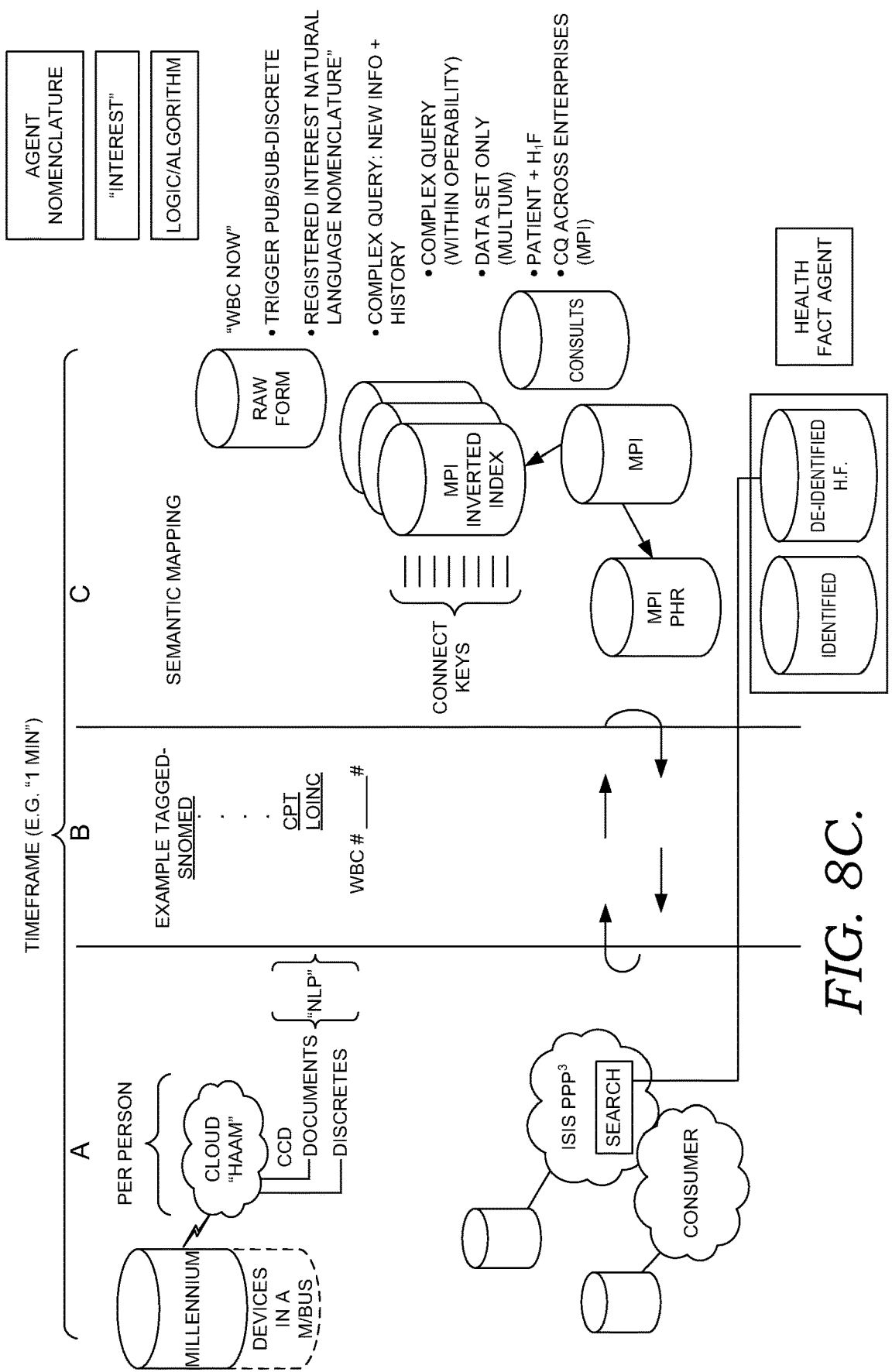

Turning now to FIGS. 8A, 8B, and 8C, a method of transforming health information and exemplary frameworks for supporting a health information transformation system are provided. It will be understood by those of ordinary skill in the art that the arrangement shown in FIG. 8B and in 8C is merely exemplary. At a high level, in some embodiments data from disparate sources is received, indexed, and stored. Based on the data, software functions, routines, or agents, referred to as observers or map reducers, may be invoked to carry out specialized processes on the data. The data is then transformed to be made usable as a one record. Once the data has been transformed into the one record, it is usable by various applications and services such as, for example, population health services, research, consumer engagement, provider interaction, and sponsors (not shown). In some instances these applications or services result in new patient data, which, in some embodiments, enters the system again as disparate data. Thus an example framework embodiment (such as depicted in FIG. 8B) is circular in that as new data is received, or becomes available (such as in the case of data mining of historical information) it is fed back into the system.

With reference to FIG. 8A, a flow diagram is provided illustrating an embodiment of a method for generating a standardized patient record (also referred to as a "one record"), herein referred to generally as method 800. At a step 821, health information is received. In embodiments, this information is considered to be "raw information" which has not been processed or transformed into a one record format. (Although in some instances, or for some types of data, the information may in fact already be in a one-record style format, structure, ontology or vocabulary, in which case only minimal processing (such as indexing, record linkage, and/or reconciliation) may be needed.

In some embodiments the information received is real-time, near-real-time, or contemporary, such as patient information from a recently performed lab test or newly inputted patient information. In some embodiments, the information received is historical information already logged and stored on various health record databases. In some embodiments, both contemporary information and historical information is received.

In some embodiments, software routines or software agents known as "crawlers," which may be embodied as and perform functions of data collectors 204 of FIG. 2, access (crawl) information at various health-information sources. In embodiments, health sources can include various EHRs, HIEs, pharma data, claims data, provider or patient provided data, observational data, lab and testing results data, patient monitors or sensors, including monitors or sensors that provide an ongoing or periodic stream (or feed) of patient data, health-information data stores or platforms, such as Cerner Millennium (Trademark) developed by Cerner Corporation, other health-information sources as described above, or any source of patient information or health information) to extract health information. In many scenarios the received health information is not universally recognizable and may use separate or proprietary coding, terms, ontologies, data formats or languages (including medical, computer-based, and foreign spoken languages). In some cases, the same medical organization or source of information may have disparate EHR systems operating within its organization. In any case, embodiments receive information from sources, which might (and likely does) include sources using disparate information systems, incompatible, proprietary, non-standardized or not universally capable of being understood. In some embodiments, information is communicated from one or more sources to a "staging area" repository, and in some embodiments, this is facilitated by one or more crawlers.

In some embodiments, the staging area repository is a temporary buffer, a local or a cloud-based storage location. In some embodiments, the staging area comprises receiving component 206, of FIG. 2, and in some embodiments, staging area is a file system. In some embodiments, Apache Hadoop is used to facilitate storing the raw information in the staging area. Hadoop and Apache HBase provide a distributed hierarchical file system capable of handling very large amounts of data being received from a plurality of disparate data sources. In some embodiments, GoogleFileSystem and BigTable, or similar file system and structures may be used to provide functionality similar to HBase and Hadoop.

At step 823, in some embodiments a back-up of the received information is stored before any processing of the information occurs. Although this step is not necessary to generate a one record, it provides a back-up "pure" form of the original, received information and is sometimes referred to as a "sacred copy" of the information. In some embodiments, metadata is also stored with the sacred copy such as metadata indicating the source, data and time, or other similar metadata information derived from the received information.

Once information is received in a staging area, in some embodiments, at a step 827, the received information is indexing or reverse indexed (that is, a reverse index such as an index without trees as used by a relational database) may be generated based on the received information) to be searchable. In embodiments, not all of the received information may be used to create (or incorporated into an existing) one record. Thus it may be necessary, to index and store the received information especially so that those portions of the information which will not be processed for the one record are nevertheless still accessible in some capacity. That is, it will be appreciated that while the received information is indexed and made searchable, it may still be in a disparate form, and those portions not used for the one record may remain in a format that is not standardized or widely recognizable.

In some embodiments, the information may be parsed and natural language processing applied, which may be carried out by an agent 1035 or software routine (as described above in connection to natural language processing component 218 of FIG. 2 and method 300, of FIG. 3) to create a searchable index (or in some embodiments a reverse index). In an embodiment, Discern nCode (Trademark) is used to extract concepts, terms, and other data for indexing. For example, in an embodiment an nCode (Trademark) agent (or multiple agents operating in parallel) facilitates semantic searching, parsing, and indexing. In some embodiments step 827 is referred to as "semantic expansion."

In some embodiments, the received information is indexed and added to previously received, indexed information. The information may be indexed multiple ways to be searchable, with pointers pointing to the original raw data. For example, the information may be indexed by source, by provider, by condition such as diabetes or sepsis, by use-case, or time-period (such as date). In embodiments, the underlying raw information is not altered or the underlying data structures are unchanged. Rather a reverse index of pointers point to the raw data structures.

At a step 831, concepts or "discrete health concepts" are identified from the indexed information. In embodiments, concepts may include, for example, conditions (e.g. sepsis, diabetes); variables (e.g. blood pressure (BP), heart rate (HR), white blood cell count (wbc), temperature (TEMP); values associated with the variables (e.g. the beats per minute for the variable heart rate); patient, provider, or sponsor (such as an employer or government) information. Concepts are further described in connection component 220 of FIG. 2, and concept mapping step 840, of FIG. 8A. In some embodiments, indexing step 827 includes identifying concepts, and in some embodiments these concepts may be used for generating the searchable index; for example, searching on information associated with a patient provider, sponsor, or condition. In some embodiments, step 331 is built on an HBase-Hadoop framework.

In some embodiments, software routines or agents 1035, operate as listening agents or watchdogs by monitoring received information for certain concepts that are triggers. In embodiments, these routines or agents are referred to as observers. For example, suppose information comes in that includes temperature. A particular observer looking for a temperature concept may respond and do something, such as invoke a special agent to transform the temperature information into a preferred synonym, structure, or format. In other words, the received temperature information is detected by the observer, which triggers an event because of the detection. In some situations, observers respond quickly to newly received information to facilitate speedier patient diagnosis and treatment. For example, newly received information might indicate that a patient's condition is deteriorating and necessitate that certain treatment actions be initiated. Thus, as soon as (or shortly after) the information comes in and is observed, the observer is able invoke a response.

In other situations where the received information comprises historical records and historical data, there is not so much a need to "listen" or "watch" for key concepts in order to invoke a response. However, concepts in the information are still identified to facilitate concept mapping at step 840 and ultimately the creation of a one record. In some embodiments, the same observer routines or agents may be used at off-peak times (at night, or when they are not busy processing contemporary information) to identify concepts in historical information. In embodiments, agents or routines performing concept identification on historical information are referred to as map reducers. For example, in one embodiment, during the day, a plurality of observers (embodied as agents 1035 or routines) may be used to monitor in parallel incoming information for key concepts (such as those associated with changes in a patient condition which necessitate timely treatment action). But during the night, or when less contemporary information is being received, some of these observer routines or agents operate as "map reducers" identifying concepts in historical information, which might include information generated that day or previous 24-hour time period. In some embodiments, the observers or map reducers send protocol buffers through strings of received information to facilitate learning mappings of the information. In some embodiments, based on identified concepts and/or concept related information (such as a format of the variables or information) the observers or map reducers invoke content mapping, or more specifically invoke routines or agents, which are part of a concept mapping step 840, such as synonymic matching, ontology mapping, record linkage, or reconciliation. In some embodiments, these operations may be invoked in any order or even iteratively in order to get the information into a one-record format.

Accordingly at step 840, concept mapping is performed. In some embodiments, concept mapping is facilitated by a mapping agent, which may be invoked by an observer or map reducer. In embodiments, concept mapping may include one or more operations performing content mapping (such as synonymic matching (nomenclature mapping) and/or ontology mapping, for example), patient record linkage, and reconciliation, in any order and iteratively. As shown in method 800, step 840 includes steps 843 (perform content mapping), 845 (perform record linkage), and 847 (reconcile information). The embodiment of step 840, including steps 843, 845, and 847, is provided only as one example of an order of operations (steps 843, 845, and 847) for concept mapping.

At step 843, content mapping is performed. In some embodiments, content mapping is carried out by nomenclature and ontology mapping component 220 of FIG. 2 or by component 220 and component 222, while in some embodiments, component 222 facilitates steps 845 and/or 847 as well. In some embodiments one or more dedicated agents such as a "mapping agent" or software routines facilitate the content mapping, and in some embodiments, the mapping agent or routine invokes other routines or agents, such as learning-agents.

Content mapping step 843 may include synonym matching (or nomenclature mapping), ontology mapping, or both, in some embodiments. The result of concept mapping is to identify "what" the information represents (that is, "what it is") so that it can be mapped to a common piece of information, such as a common language, scale, or format that is universally understood, or standardized, or otherwise in a format/structure usable by the services which draw on information from the one record(s). In some embodiments, one or more synonym-discovery agents facilitate synonymy matching, and/or one or more ontology mapper agents facilitates ontology mapping. In some embodiments, these agents operate in parallel, for efficiency.

Synonym matching (or nomenclature mapping) facilitates the mapping of semantically similar terms between and among two or more information systems. In some instances, these embodiments facilitate the automatic discovery, establishment, and/or statistical validation of linkages between a plurality of different nomenclatures employed by a plurality of information systems, such as multiple electronic health record systems. Additional information about embodiments of step 843 or step 840 that include synonym matching, as it relates to our invention, is provided in U.S. application Ser. No. 13/569,781, titled "Synonym Discovery," filed Aug. 8, 2012, which is herein incorporated by reference in its entirety.

Ontology mapping provides discovery, validation, and quality assurance of nomenclatural linkages (also called 'mappings' or 'cross-walks') between pairs of terms or alternatively, combinations of terms ('morphemes' or 'termclusters') in databases that are extant on multiple different health information systems that do not share a set of unified codesets, nomenclatures, or ontologies to tag or code the documents and records, or that may in part rely upon unstructured free-text narrative content instead of codes or standardized tags. In some instances, these embodiments discover semantic structures that exist naturally in the documents and database records maintained by those systems, including relationships of synonymy and polysemy between terms used in said documents and database records arising from disparate processes and maintained by different information systems. Furthermore, some of these embodiments then utilize the discovered latent semantic structures to establish linkages between terms extant on the multiple systems or to validate linkages that have been established in other ways, either by manual human effort or by other algorithmic means. Additional information about embodiments of step 843 or step 840 that include ontology mapping, as it relates to our invention, is provided in U.S. application Ser. No. 13/645,896, titled "Ontology Mapper," filed Oct. 5, 2012, which is herein incorporated by reference in its entirety.

At step 845, record linkage (or master person (or patient) index (MPI) record linkage, is performed. Record linkage determines where two or more different pieces of information (or records) are associated with the same patient or dataset, and then links these pieces of information together. Thus, record linkage determines records that refer to the same entity or individual, or in some cases, the same dataset.

In some embodiments, the linkages may be a highly-likely-match linkage, which is a linkage of records that are highly probable to belong to the same entity. In other words, there is a higher confidence in the linkage. For this type of linkage, it is desirable to have a higher confidence because the consequence of mistaking the record for the patient might result in the patient being harmed, for example based on a treatment administered because of the linkage. In some embodiments, these linkages are reviewed by a human expert before a linkage is established.

In some embodiments, the linkages may be "pseudo-linkages" wherein records are not determined to be a perfect match, necessarily. (In other words, the probability of that the records belong to the same patient is lower than a level, closer to 100% that is needed to confidently conclude that the records are for the same patient.) Pseudo-linkages facilitate research studies by building out more complete patient records that may be analyzed by various services (discussed in connection to FIG. 8B). For example, pseudo-linkages may be used for conducting virtual clinical trials.

Virtual clinical trials, like clinical trials, may be used to determine the effect of an exposure (such as a drug or treatment) on patients having a particular condition, identify changes such as improvement or deterioration resulting from some event (such as a change in activity, medication, treatment or other patient exposure) or for other purposes like clinical trials. But unlike clinical trials, virtual clinical trials may be performed using historical patient information. For example, by building a one record for a population of patients, and examining the historical information contained therein, it may be determined that certain patients who received drug X following a procedure faired significantly better than patients who were not exposed to drug X.

Additional information about embodiments of step 845 or step 840 that include record linkage, as it relates to our invention, is provided in U.S. Provisional Application No. 61/641,097, titled "System And Method For Record Linkage," filed May 1, 2012, which is herein incorporated by reference in its entirety.

At a step 847, the information is reconciled. In some embodiments, reconciliation includes eliminating duplicative information; cleansing the information (such as removing outliers; for example, a patient's temperature of 1000 degrees); filling in holes in patient information through record linkage or identifying missing information and accessing (or soliciting) needed information to fill the hole; correcting information such as inconsistent information (For example, where several parts of a patient's record indicate that the patient was born on a certain date, and one part of a patient's record shows a slightly different date, then identifying that date as a likely error to be reconciled) or other operations to correct, restore, and/or complete patient information. For example, duplicative or redundant information might occur where information comes in from two sources, for example from a patient temperature sensor and from a doctor's note observing the sensor. In this example, if two temperature-related pieces of information are received (at step 821), it would be an error to interpret this as two different temperatures. Rather they are the same temperature information, but provided twice. Thus in some embodiments, reconciliation step 847 eliminates the redundant temperature information from being included in the one record.

In some embodiments, reconciliation is carried out by one or more software routines or agents, including learning agents, which may be dedicated reconciliation agents. In some embodiments, reconciliation rules, which may come from rules 1010 of FIG. 10A, are employed. In some embodiments, reconciliation procedures occur at various points within concept mapping step 840, or within the steps of step 840, such as within content mapping step 843, before or after synonym matching or ontology mapping.

In some embodiments, some or all of steps 821, 827, 831 and 840 include aspects of method 300 described above. For example, in some embodiments at step 831 a determination is made about whether the received data is structured or unstructured and which processes of processes 310, 308, and 306 need to be leveraged to transform the information into a unified standardized "one record." Likewise, as described in steps 306, 308, and 310 ontology mapping and nomenclature mapping (also referred to as synonymy matching or mapping) are carried out at content mapping step 843, and distributed adaptive knowledge processing can comprise record linkage step 845 and/or reconciliation step 847, in some embodiments.

At a step 851, the processed patient information outputted from concept mapping step 840 is stored as (or updated to) a one record for a patient. In some embodiments, where a one record associated with a patient does not yet exist, the processed information is stored as a one record. In scenarios where the one record already exists, then the one record is updated by adding the processed information. In some embodiments, reconciliation may be performed again to ensure that redundant information is not being added to the one record. In some embodiments such as the circular scenario described above where a one record already exists for a patient, services using the one record may output or lead to the output of new raw information, to be added to the one record. In such embodiments, the processed new patient information outputted from concept mapping step 840 is stored to an existing one record, thereby updating the one record.

With reference to FIGS. 8B and 8C, exemplary frameworks of a health information transformation system are provided. As described above, at a high level, data from disparate sources comes into the system, and is initially crawled, indexed, processed and mapped and stored to be made usable as a one record, in some embodiments. Once the data has been mapped into the one record, it is usable by various applications and services such as, for example, population health services 870, research services 880, consumer engagement services 865, provider interaction services 860, and sponsors services (not shown). In some instances these applications or services result in new patient data, which, in some embodiments, enters the system again as disparate data (at 810). Thus the example embodiment depicted in FIG. 8B is circular in that as new data comes in, or becomes available (such as in the case of data mining historical information) it is fed back into the system.

In embodiments, components 810 through 850 of FIG. 8B correspond to the steps of method 800, of FIG. 8A. With continuing reference to FIG. 8B, in some embodiments, data initially comes at in from disparate sources (at 810) such as Cerner Millennium, EMR2, Claims, and HIE, pharmaceutical data, for example, or other sources described previously. The data first enters a staging area 820, which in embodiments may be as described in step 821 of method 800. There the data is stored so that it is preserved. Metadata such as the source, date, or other metadata information is also stored.

At 825, the data is indexed into a searchable index, such as described in step 827 of method 800. The indexing may occur multiple ways, and in some embodiments takes the form of an inverted index with pointers to the raw data. In some embodiments the data is first applied to a natural language parsing algorithm or software agent, such as nCode to extract concepts from natural language expressions. In some embodiments, the indexing step is performed using Apache Hadoop, which provides a distributed file system.

As mentioned above, unstructured or raw data is converted from human speech or input into a computer-useable language using a natural language processing component. An exemplary natural language processing system may include Discern nCode™ by Cerner. By way of illustrative example, a natural language processing component, which may be implemented as a software agent, scans a physician's dictated note and identifies clinical concepts with codified meanings. For example, a physician's note pertains to a patient who has previously been diagnosed with diabetes and is now suffering from diabetic retinopathy. Natural language processing component identifies the clinical concept "diabetic" and the clinical concept "retinopathy." Both of these terms have an established codified (i.e. ICD-9-CM code) meaning. Next, the natural language processing component labels the identified clinical concepts as positive, suspected, or negative based on the analysis, understanding, and context of the text within the note. In this case, the clinical concepts "diabetic" and "retinopathy" would both be labeled positive. The natural language processing component then translates the clinical concept into a health concept. Using the example given above, the clinical concept "diabetic" plus "retinopathy" is translated into a health concept "diabetic retinopathy" by applying the correct ICD-9-CM codes and the standard SNOMED nomenclature. The health concept "diabetic retinopathy" is now considered structured data and may be indexed. In some embodiments the indexed data is stored and preserved.

At 830, in some embodiments, the data is then processed by observers or map reducers, or both, as described in connection to step 831 of method 800. Observers are software functions or software agents that function like watchdogs and come into action upon triggering events. For example, patient data suggesting a particular condition, treatment history, or health care provider preference may invoke an observer to further process the data or invoke other actions or agents. In some embodiments, an observer may process concurrent information such as information being received from a patient bedside monitor or being received from the patient. In some embodiments protocol buffers are applied to the data.

At 840, concept mapping processes the indexed data into a format usable as one-record data, as described at step 840 of method 800. In some embodiments, concept mapping includes one or more functions for mapping, reconciliation, record linkage. In some embodiments these functions are carried out by software agents, and in some embodiments these agents are learning agents. Mapping functions determine what the data is; that is, mapping resolves the data to a common language, scale, or metric so that it may be understood by applications and services. For example, temperature data may be mapped to a common scale.

Record linkage (or MPI record linkage), which may be an operation performed within 840, resolves data as belonging to the same person or dataset. Thus two records about the same person may be combinable into a single record, as a result of record-linkage. As described in connection to step 845 of method 800, in some embodiments, record linkage includes two types of record linkage; pseudo-mapping, which doesn't have to be exactly accurate and perfect matches or highly-likely-matches, which in some embodiments apply rules, such as rules provided by institutions, in order to determine whether records should be linked. For example, a rule may be that where the last name, address, and social security number match, then the records should be identified as belonging to the same person. In some embodiments, the record linkage produces one or more suggestions which are then reviewed by an actual person before being linked.

Reconciliation operations, which may be a part of 840, cleanse the data by, for example, eliminating duplicates, such as the same data from different sources, and removing outliers, and are further described in connection to step 847 of method 800. Where more than one of mapping, record-linkage, and/or reconciliation functions are employed, the order can vary, in embodiments, and also in instances of processing the data, based on the specific data being processed, although typically some reconciliation may be necessary after the mapping or record linkage functions.

At 850, the output of the concept mapping at 840 is stored as the one record. In embodiments, one record data includes data necessary to understand and represent the patient for applications and services associated with health-care treatment, management, research, and monitoring, for example. In embodiments, information within a one record includes transformed (processed) data received from the disparate sources, pointers to raw data or other processed or transformed data, or a combination of pointers and data. Thus for example, in some embodiments, it may be unnecessary to store 10-year old vital-sign information about a patient in the one-record, but this information, if available, may be stored at its original location and made accessible, via address or pointer, through the one record. So the information nevertheless remains accessible, in some embodiments. Other information of the one record may include demographic results, medical profiles, and other information needed to understand and represent the patient, in embodiments.

The format, structure, and ontology of the one record is intended to be standardized, universally recognizable, or recognizable by applications and services that use information of the one record. For example, in an embodiment, a one record uses standard vocabularies. In embodiments, the one-record may actually represent a one-record record for each of a plurality of patients. In some embodiments, the one record is embodied using an Oracle database, and in some embodiments, as an Oracle transactional database.

Many applications and services (860, 865, 870, and 880, for example) are made possible or facilitated through embodiments of the one record. For example, information from multiple one-records may be used for conducting virtual clinical trials on treatment of patients, as described above in connection to step 840 of method 800. In particular, by making available information that was previously inaccessible or unknown, through historical or concurrent data sources, it is possible to gather and analyze information about only certain patients having certain conditions and treated certain ways. For example, a particular physician may have a much higher rate reduced complications following a certain medical procedure. By mining one-record derived patient data from patients undergoing this procedure, it can be possible to determine what actions this particular physician is performing that are unlike actions performed by other physicians performing the same procedure, or what other information is different about these patients, than other patients undergoing the same procedure.

In some embodiments, information is accessed from one record 850 by ETL (extraction, transform, and load) which provides reduced read of the data. For example, if there are one million results, they can be aggregated so that it is not necessary to perform 1 million reads each of a row of information.

Applications and services 870 include identified population health information. (In other words, patients are identifiable, based on information contained herein, for example in personal health records.) Applications and services (Research) 880 includes de-identified patient information. (In other words, it is not possible or highly difficult to determine patient identity from the information contained herein, for example the information stored within 880 in the Cerner Health Facts (Trademark) database.) In some embodiments, information is de-identified by anonymization, such as by removing identifying information and/or slightly altering innocuous but identifying information such as dates of birth or dates of testing or operations.

Provider interaction services 860 includes services for facilitating provider efficiency and optimization. For example, in some instances providers are evaluated based on the number of re-admissions. So the provider may need to alter work flows or perform other changes (such as implementing home health programs or visiting programs) to reduce readmission rates. In some embodiments, other services include statistics for understanding readmission rates and suggestions for reducing readmission, cost controls, evaluation of existing services and applications, load balancing, identifying at-risk patients (for example patients at risk for sepsis), or application portals enabling providers to make better decisions by managing treatment more efficiently.

Although not shown in FIG. 8B, other services and applications such as sponsor services and applications are facilitated by the one record 850. A sponsor might be an employer, government, non-profit organization, or agency. As with the provider, the sponsor may be interested in improving efficiency and optimization.

Consumer engagement services 865, which in embodiments accesses the one record 850 directly (not shown) or through provider interaction component 860, includes services for facilitating consumer interaction in managing their own health care or the health care of others, for example a family member. Example applications and services might include healthy living incentives or rewards programs, consumer questionnaires such as self-diagnosis questionnaires, or other consumer oriented health-management applications. In some embodiments, these applications and services may use information from a one record associated with the consumer, or these applications and services may generate new information to be included into a one record associated with the consumer. For example, where a patient seeking advice completes a health questionnaire, newly provided information may be incorporated (such as via method 800) into the patient's one record. Moreover, in some embodiments, where this patient meets certain criteria (such as having had a recent visit or no chronic conditions, for example), the patient may receive advice without having to schedule a visit with a doctor. In this embodiment, the advice provided to the patient, which may be provided by a software agent pr routine, through an interface such as interface 1040, can be based on the updated one record (the one record with information from the questionnaire).

As described above, where services and applications such as 860, 865, 870, and 880 generate new patient information or cause new patient information to be generated (for example, contributes to causing a patient-related event or action that ultimately leads to new patient information), that new information may become part of 810, and subsequently processed (such as by way of method 800) to become part of the one record.

Continuing with FIG. 8B, knowledge base 882 comprises learned information, rules, content parameters for agents, best practices, and similar information obtained from 880 or 870 (not shown), and in some embodiments is accessible to agent library 890. Agent library 890 includes agents, which facilitate decision support services and creation (or update) of the one record. For example, mapper agents, record-linkage agents, or sepsis agents, as described in FIG. 9. In some embodiments, agents of agent library 890 post outcomes, make recommendations, or provide alerts, such as the example sepsis agent described in FIG. 9.

FIG. 8C provides another aspect of a framework like the one provided in FIG. 8B, where section A includes raw information being received, section B corresponds to indexing the information, and section C corresponds to concept mapping (such as semantic mapping).

Figure 9:
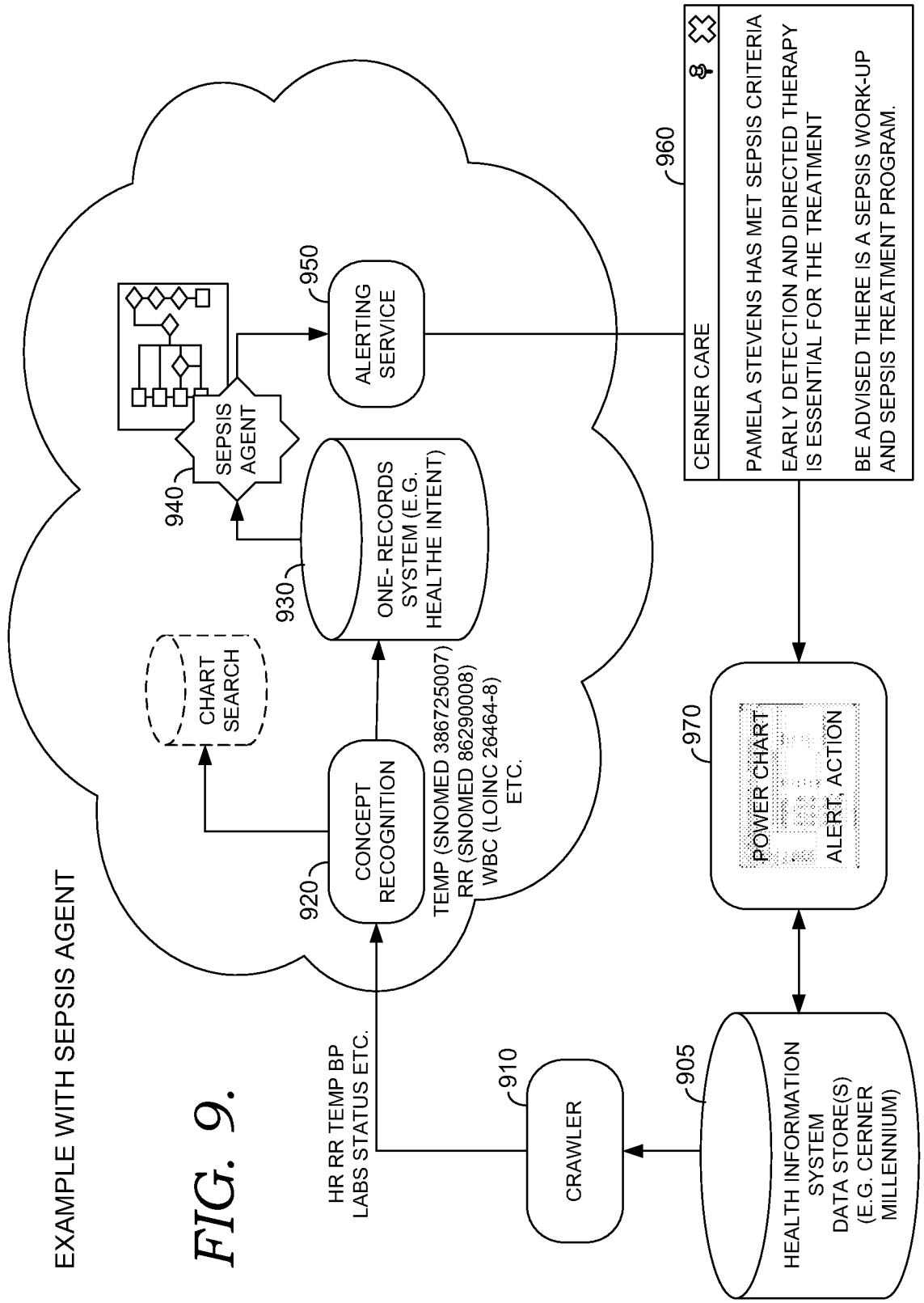
FIG. 9 depicts a example embodiment of a method to transform health information for detecting sepsis, in accordance with an embodiment of the invention.

Turning now to FIG. 9, an example implementation of an embodiment of a health information transformation system is illustratively provided. In particular, an example embodiment is provided wherein the one record facilitates detection of sepsis in a patient earlier than what might otherwise occur without having a one record. In many situations, for a particular patient with a condition such as sepsis, the patient's symptoms manifested at any one moment (such as one "observation" which may be captured and recorded in a health record) is insufficient or more difficult for accurately diagnosing the patient's condition, then having information received from multiple observations, such as may occur if the patient has visited their regular doctor, an emergency room, an urgent care center, or other care provider. However, where the information from these multiple observations is captured and recorded in disparate EHRs or other data systems, it may not be possible for a health care entity to timely access the information in order to detect sepsis, let alone a risk for developing sepsis. Accordingly, having a one record facilitates timely detection of sepsis, by for example, a "sepsis agent" designed to detect sepsis and invoke a response, such as by issuing an alert.

Continuing with FIG. 9, data store 905 comprises one or more sources of health information for a patient. In some embodiments, the information includes information from disparate sources. For instance, a patient may have an electronic health record (EHR) with his or her primary care physician, but this EHR may not be shared with any other medical organizations that are involved with treating the patient, such as an emergency room, an urgent care clinic, a specialist, etc. As such, patient information is typically not shared between facilities, which may impair clinicians in their treatment of patients, as clinicians are unable to see the full scope of the patient's current medical conditions. For example, a patient may have a primary care physician, but may have an urgent medical situation and may go to an urgent care clinic one day and to an emergency room the next day for complications from a procedure performed by a specialist. This scenario is commonplace. Additionally, the case is rare when a patient is seen and treated by multiple clinicians who all use a common medical record system. Moreover, the monitoring for and detection of certain conditions, such as Sepsis, can involve inputting diverse reference ranges of monitored variables by different health care providers, which can result in different outcomes, i.e., this patient is or is not developing Sepsis, from using the different reference ranges. In one embodiment, data store 905 comprises Cerner's Millennium (Trademark) system.

At 910, health information in 905 is crawled (or accessed) and received. In some embodiments, the health information is received as described in connection to step 821 of method 800. At 920, concept mapping, such as described at step 840 of method 800, is performed and concepts are recognized from the information. In the example embodiment provided in FIG. 9, steps 920 through 950 may be performed in the "cloud" (as shown) on cloud computing platform 162. At step 930 a one record is created (or updated) from the recognized (mapped) concepts at 920. In some embodiments, the one record is part of Cerner's Health Intent (trademark) health records system. A sepsis agent 940 runs and detects a likelihood of sepsis for a particular patient. Additional information about embodiments sepsis agent 940, sepsis detection (or other chronic condition detection) using one or more sepsis (or other detection) agents, and aspects of information crawling and concept mapping for detecting sepsis (or other chronic conditions) is provided in U.S. Provisional Application No. 61/681,446, titled "Clinical Decision Support for Sepsis," filed Aug. 9, 2012, which is herein incorporated by reference in its entirety.

Upon detecting a likelihood of sepsis, alerting service 950 is invoked. In some embodiments, sepsis agent 940 invokes alerting service 950. In some embodiments, alerting service 950 comprises one or more alert agents or software routines. In some embodiments, an agent or agents running on cloud platform send alert or notice outcome 960 back to an information source associated with the patient, such as the EHR associated with the patient's primary care physician. For example, in an embodiment, alerting service sends an alert 960 to Cerner Millennium (Trademark), where it can be seen by a health care provider and/or care taker. In some embodiments, once the alert is received at the source, which might be a hospital, an expert rule is run (or an agent invoked) to determine who should be notified about the detection of sepsis (such as the patient, family members, care taker, health care provider, or similar entity) and how that person (or those people) should be notified, such as by text message, alarm, call, email, scheduling an appointment, leveraging an electronic chart such as Cerner PowerChart (Trademark) to provide notice, or other way.

At 960, an example alert is provided, issued by alerting service 950. In this example, the alert indicates that patient Pamela Stevens has met sepsis criteria (described in connection to sepsis agent 940). A recommendation is provided, that early detection and directed treatment is essential for treating sepsis, and that there is a sepsis work-up and treatment program. At 970, the example alert 960 is shown inputted into a care-provider associated user interface such as an electronic chart, for example Cerner's PowerChart, where it is viewable by a health care provider. In embodiments, the alert and/or other outcome information resulting from the detection of sepsis criteria by sepsis agent 940, can be communicated to one or more of the sources associated with the patient, where it, as well as other new information resulting from it (such as results of new tests, observations, or other health information not previously considered for incorporation into the one record) may be subsequently crawled and incorporated into a one-record.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more non-transitory computer hardware devices having computer-executable instructions embodied thereon, that, when executed, implement a method for transforming raw healthcare data into usable healthcare data, the method comprising:
   receiving raw health information from at least one data collector, the data collector accessing the raw health information from one or more raw data sources;
   indexing a portion of the raw health information to create a searchable index;

transforming the indexed portion of the raw health information into usable data corresponding to a patient, using one or more content-mapping services, the transforming comprising:
  (1) sorting the portion of the raw health information into structured data of standard nomenclature, structured data of non-standard nomenclature, and unstructured raw data;
  (2) when the portion of the raw health information is unstructured raw data, identifying a first discrete clinical concept having an associated codified meaning and a second discrete clinical concept without a codified meaning via natural language processing, the first and second discrete clinical concepts identified based on a level of detail in the unstructured raw data;
  (3) transforming the first discrete clinical concept into a first health concept that is structured data of standard nomenclature by applying the associated codified meanings, and transforming the second discrete clinical concept into a second health concept that is structured data of standard nomenclature by associating the second discrete clinical concept with a broader health concept having the codified meaning, the codified meaning and the associated codified meaning based on one or more standardized clinical codes; and
  (4) mapping the first and second health concepts to a relevant piece of information based on nomenclature and ontology mapping, the ontology mapping providing discovery of nomenclatural linkages between pairs of terms or combinations of terms that are extant on multiple different health information systems, at least two of the different health information systems not sharing at least one of a set of unified codesets, nomenclatures, or ontologies to tag or code the documents and records;
storing the usable data into a data repository; and
utilizing the usable data by a computer application to perform a content-mapping, the content-mapping service comprising a synonymic-discovery service or an ontology mapping service.

2. The non-transitory computer hardware devices of claim 1, further comprising storing a sacred copy of the received raw health information.

3. The non-transitory computer hardware devices of claim 1, wherein mapping the first and second concepts to the relevant piece of information further comprises performing record linkage on the portion of the raw health information.

4. The non-transitory computer hardware devices of claim 3, wherein mapping the first and second health concepts to the relevant piece of information further comprises performing reconciliation on the portion of the raw health information, and wherein performing reconciliation comprises eliminating duplicative information, removing outliers, filling in holes, or correcting inconsistent information.

5. The non-transitory computer hardware devices of claim 1, wherein at least one of the ontology-mapping service and the synonymic-discovery service are carried out by a software agent.

6. The non-transitory computer hardware devices of claim 1, wherein indexing the portion of the raw health information includes natural-language processing of the portion of the raw health information.

7. The non-transitory computer hardware devices of claim 1, wherein the transforming further comprises labeling each discrete clinical concept as positive, suspected, or negative based on context of text in the portion of raw health information identified via natural language processing.

8. The non-transitory computer hardware devices of claim 7, wherein labeling each discrete clinical concept comprises: identifying discrete clinical concepts with codified meanings, and based on a degree of confidence in the identification, assigning a label to each discrete clinical concept, the label indicating each of the discrete clinical concepts as one of positive, suspected, or negative.

9. The non-transitory computer hardware devices of claim 1, wherein the relevant piece of information comprises data represented by a standardized structure, nomenclature, format, or ontology.

10. The non-transitory computer hardware devices of claim 1, wherein the one or more raw data sources comprise at least two disparate sources.

11. The non-transitory computer hardware devices of claim 1, wherein the at least one data collector comprises at least one of an electronic health record crawler, a clinical and administrative data collector, a claims data collector, a document feed collector, or a medical device feed collector.

12. The non-transitory computer hardware devices of claim 1, wherein the raw health information comprises historical health information.

13. The non-transitory computer hardware devices of claim 1, wherein the computer application includes a virtual clinical trial.

14. A system for transforming raw healthcare data into relevant healthcare data, the system comprising:
a staging area repository for receiving raw health information from at least a first source of a plurality of sources of raw health information;
one or more processors;
memory, the memory comprising:
  a crawler agent for accessing the raw health information from the first source and providing a copy of the raw health information to the staging area;
  an observer agent for identifying a plurality of discrete clinical concepts with corresponding clinical codes from the copy of raw health information in the staging area; and
  a concept mapping agent for transforming a portion of the copy of raw health information into relevant data associated with a patient based on the identified concepts using one or more content mapping services, the transforming comprising:
    (1) sorting the portion of the raw health information into structured data of standard nomenclature, structured data of non-standard nomenclature, and unstructured raw data;
    (2) when the portion of the raw health information is unstructured raw data, identifying a plurality of discrete clinical concepts represented in non-standard nomenclature using a natural language processing component;
    (3) labeling each of the plurality of discrete clinical concepts as one of positive, suspected, or negative based on context of text in the portion of raw health information identified using the natural language processing component;
    (4) transforming the plurality of discrete concepts into a plurality of health concepts by associating the plurality of discrete clinical concepts with broader health concepts having codified meanings and applying the codified meanings to the plurality of discrete clinical concepts, the codified meanings based on one or more standardized clinical codes; and (5) mapping the plurality of health concepts to a relevant piece of information based in existing relationships within a nomenclature and ontology mapping component, the nomenclature and ontology mapping component associating the plurality of health concepts to one or more broader health concepts, the one or more broader health concepts being structured data of standard nomenclature suitable for processing by a distributed adaptive knowledge engine component; and a data repository for storing the relevant data, at least one content-mapping service comprising a synonymic-discovery or an ontology mapping service.

15. The system of claim 14, wherein the data repository is accessible to a software application or service component.

16. The system of claim 14, wherein the concept mapping agent is configured for performing a reconciliation service on the portion of the copy of raw health information, including at least one of eliminating duplicative information, removing outliers, filling in holes, or correcting inconsistent information.

17. The system claim 15, wherein the software application comprises an application for facilitating performing virtual clinical trials on the relevant data.

18. One or more non-transitory computer hardware devices having computer-executable instructions embodied thereon, that, when executed, implement a method for generating a universal patient health record, the method comprising:

receiving raw health information from one or more data sources;

from the received raw health information, identifying a plurality of health concepts, the identifying comprising:
(1) sorting the portion of the raw health information into structured data of standard nomenclature, structured data of non-standard nomenclature, and unstructured raw data;
(2) when the portion of the raw health information is unstructured raw data, identifying a plurality of discrete clinical concepts represented in non-standard nomenclature via natural language processing;
(3) labeling each of the plurality of discrete clinical concepts as one of positive, suspected, or negative based on context of text in the portion of raw health information identified via natural language processing; and
(4) transforming the plurality of discrete clinical concepts into the plurality of health concepts by associating the plurality of discrete clinical concepts with broader health concepts having codified meanings and applying the codified meanings to the plurality of discrete clinical concepts, the codified meanings based on one or more standardized clinical codes;

based on the identified plurality of health concepts, transforming at least a portion of the raw health information into relevant data associated with a patient, the transforming comprising:
(1) performing content mapping on the portion of the raw health information using one or more content-mapping services including at least one of a synonymic-discovery service or an ontology mapping service, the ontology mapping service providing discovery of nomenclatural linkages between pairs of terms or combinations of terms that are extant on multiple different health information systems, at least two of the different health information systems not sharing at least one of a set of unified codesets, nomenclatures, or ontologies to tag or code the documents and records; or
(2) performing patient record linkage on the at least the portion of the raw health information; and storing the relevant data into a data repository, thereby creating the universal patient health record;

the transformed relevant data comprising data represented by a standardized structure, nomenclature, format, or ontology.

19. The non-transitory computer hardware devices of claim 18, wherein performing content mapping further comprises performing reconciliation on the portion of the raw health information, and wherein performing reconciliation comprises eliminating duplicative information, removing outliers, filling in holes, or correcting inconsistent information.

20. The non-transitory computer hardware devices of claim 18, wherein at least one of the ontology-mapping service and synonymic-discovery service are carried out by a software agent.

* * * * *

UNITED STATES PATENT AND TRADEMARK OFFICE
CERTIFICATE OF CORRECTION

PATENT NO. : 10,628,553 B1
APPLICATION NO. : 13/647187
DATED : April 21, 2020
INVENTOR(S) : John Christopher Murrish et al.

Page 1 of 1

It is certified that error appears in the above-identified patent and that said Letters Patent is hereby corrected as shown below:

On the Title Page

Page 4, item [56], Column 1, Line 20: Delete "Eidemiological" and replace with --Epidemiological--.
Page 4, item [56], Column 1, Line 46: Delete "Schook" and replace with --School--.

In the Drawings

Sheet 2 of 14, FIG. 1B., Reference Numeral 166: Delete "ASSESSEMENT" and replace with --ASSESSMENT--.

In the Specification

Column 2, Line 34: Delete "invention." and replace with --invention;--.
Column 2, Line 41-42: Delete "invention." and replace with --invention;--.
Column 10, Line 12: Delete "cloud" and replace with --cloud.--.
Column 13, Line 60: Delete "Kohenen" and replace with --Kohonen--.
Column 13, Line 62: Delete "Naives" and replace with --Naive--.
Column 18, Line 21: Delete "for the of patient information collection" and replace with --for the collection of patient information--.
Column 40, Line 32: Delete "pr" and replace with --or--.
Column 41, Line 50: Delete "Health" and replace with --Healthe--.

In the Claims

Column 43, Line 20: Delete "meanings," and replace with --meaning,--.
Column 45, Line 23: After "system" please insert --of--.

Signed and Sealed this
Fourteenth Day of July, 2020

Andrei Iancu
*Director of the United States Patent and Trademark Office*